(12) United States Patent
Tanifuji et al.

(10) Patent No.: US 8,207,189 B2
(45) Date of Patent: Jun. 26, 2012

(54) COMPOUND HAVING AFFINITY FOR AMYLOID

(75) Inventors: Shigeyuki Tanifuji, Sodegaura (JP);
Daisaku Nakamura, Sodegaura (JP);
Shinya Takasaki, Sodegaura (JP); Yuki Okumura, Sodegaura (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 333 days.

(21) Appl. No.: 12/312,867

(22) PCT Filed: Aug. 16, 2007

(86) PCT No.: PCT/JP2007/065955
§ 371 (c)(1),
(2), (4) Date: May 29, 2009

(87) PCT Pub. No.: WO2008/065785
PCT Pub. Date: Jun. 5, 2008

(65) Prior Publication Data
US 2010/0069640 A1  Mar. 18, 2010

(51) Int. Cl.
C07D 471/04 (2006.01)
A61K 31/44 (2006.01)

(52) U.S. Cl. ................................ 514/300; 546/121
(58) Field of Classification Search .............. 514/300; 546/121
See application file for complete search history.

(56) References Cited

U.S. PATENT DOCUMENTS

| | | |
|---|---|---|
| 4,727,145 A | 2/1988 | Press |
| 4,871,745 A | 10/1989 | Press |
| 5,658,857 A | 8/1997 | Andreee et al. |
| 6,045,773 A | 4/2000 | Isakson et al. |
| 6,562,579 B1 | 5/2003 | Yu et al. |
| 6,596,731 B2 | 7/2003 | Mutel et al. |
| 6,713,042 B2 | 3/2004 | Liu |
| 6,916,826 B2 | 7/2005 | Mutel et al. |
| 7,186,714 B2 | 3/2007 | Gudmundsson et al. |
| 7,425,318 B2 | 9/2008 | Kung et al. |
| 2002/0188128 A1 | 12/2002 | Mutel et al. |
| 2004/0180921 A1 | 9/2004 | Mutel et al. |
| 2005/0182059 A1 | 8/2005 | Winzenberg et al. |
| 2005/0228004 A1 | 10/2005 | Gudmundsson et al. |
| 2005/0260126 A1 | 11/2005 | Kudo et al. |
| 2006/0051293 A1 | 3/2006 | Kung et al. |
| 2009/0252679 A1* | 10/2009 | Tanifuji et al. ............ 424/1.89 |
| 2010/0249418 A1* | 9/2010 | Tanifuji et al. ............ 546/121 |
| 2010/0249419 A1* | 9/2010 | Tanifuji et al. ............ 546/121 |
| 2010/0292479 A1* | 11/2010 | Tanifuji et al. ............ 546/121 |

FOREIGN PATENT DOCUMENTS

| | | |
|---|---|---|
| CN | 1117732 A | 2/1996 |
| CN | 1518550 A | 8/2004 |
| CN | 1529597 A1 | 9/2004 |
| EP | 0261912 A2 | 3/1988 |
| EP | 2019103 B1 | 1/2009 |
| EP | 2022792 A1 | 4/2009 |
| EP | 2042501 A1 | 4/2009 |
| JP | 2001-43978 | 2/2001 |
| JP | 2002-512945 | 5/2002 |
| JP | 2002-523383 A | 7/2002 |
| JP | 2004-506723 A | 3/2004 |
| JP | 2004-525192 | 8/2004 |
| JP | 2004-525192 A | 8/2004 |
| JP | 2005-504055 A | 2/2005 |
| JP | 2005-512945 A | 5/2005 |
| WO | 94/18198 A | 8/1994 |
| WO | WO 99/55304 | 11/1999 |
| WO | WO 00/10614 A1 | 3/2000 |
| WO | 01/74813 A2 | 10/2001 |
| WO | WO 01/74813 A2 | 10/2001 |
| WO | WO 01/74815 A1 | 10/2001 |
| WO | WO 02/16333 A2 | 2/2002 |
| WO | 02/085903 A | 10/2002 |
| WO | 02/085903 A2 | 10/2002 |
| WO | 02/092086 A1 | 11/2002 |
| WO | WO 02/092086 A1 | 11/2002 |
| WO | 03/000689 A | 1/2003 |
| WO | WO 03/018070 A1 | 3/2003 |
| WO | WO 2004043497 A1 | 5/2004 |
| WO | WO 2005/066177 | 7/2005 |
| WO | WO2005/066177 | 7/2005 |

OTHER PUBLICATIONS

Liu et al., Synthetic Communications (2004), 34(2), 361-367.*
Sarkar et al., Neuroscience, (Oct. 27, 2011) vol. 194, pp. 241-249.*
Zhi-Ping Zhuang et al: "Structure-activity Relationship of Imidazo[1,2-a]pyridines as Ligands for Detecting beta-Amyloid Plaques in the Brain" Journal of Medicinal Chemistry, American Chemical Society, Washington, US, vol. 46, Jan. 1, 2003, pp. 237-243, XP002446716 ISSN: 0022-2623.

(Continued)

Primary Examiner — Niloofar Rahmani
(74) Attorney, Agent, or Firm — Fitch, Even, Tabin & Flannery, LLP

(57) ABSTRACT

A compound represented by the following formula or a salt thereof:

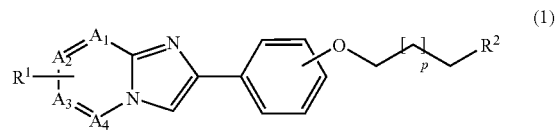

(1)

wherein each of $A_1$, $A_2$, $A_3$ and $A_4$ independently represents a carbon or nitrogen, $R^1$ is a radioactive halogen substituent, $R^2$ is a group selected from the group consisting of hydrogen, a hydroxyl group, a methoxy group, a carboxyl group, an amino group, an N-methylamino group, an N,N-dimethylamino group and a cyano group, and p is an integer of 0 to 2, provided at least one of $A_1$, $A_2$, $A_3$ and $A_4$ represents a carbon, and $R^1$ binds to a carbon represented by $A_1$, $A_2$, $A_3$ or $A_4$, is effective as an image diagnosis probe targeting amyloid. A diagnostic agent for Alzheimer's disease contains the compound.

16 Claims, 5 Drawing Sheets

OTHER PUBLICATIONS

Supplementary European Search Report issued on Apr. 1, 2010 in European Application No. 07792585.7.
Written Opinion issued Jul. 30, 2010, in corresponding Singapore Application.
Pauline J. Sanfilippo et al., "Synthesis of (Aryloxy)alkylamines. 2. Novel Imidazo-fused Heterocycles with Calcium Channel Blocking and Local Anesthetic Activity", J. Med. Chem. 1988, 31, pp. 2221-2227.
Examination Report issued Aug. 6, 2010, in corresponding New Zealand Application.
Office Action, apparently issued on Nov. 3, 2010, apparently in Chinese application 200780021402.8.
Examination Report issued in counterpart New Zealand Application 577511.
Office Action issued Apr. 27, 2011, corresponding with IL Application No. 209651.
Office Action issued Apr. 27, 2011, corresponding with IL Application No. 209650.
Office Action issued Apr. 27, 2011, corresponding with IL Application No. 209649.
Office Action issued May 15, 2011, corresponding with Chinese Application No. 200780021402.8.
Office Action, with translation, issued Nov. 24, 2011 in Chinese Application 200880123407.6.
Chun-xiong Lu et al, Synthesis and Biodistribution of β Amyloid Plaques Imaging Agent 131I-IMPY, Journal of Nuclear and Radiochemistry, col. 2, No. 4, pp. 232-235 (Nov. 2005) abstract at p. 235.
Israel Office Action, dated Oct. 9, 2011, Ministry of Justice Patent Office, corresponding with Patent Application No. 198995.
John A. Hardy et al., "Alzheimer's Disease: The Amyloid Cascade Hypothesis", Science, vol. 256, Apr. 10, 1992, pp. 184-185.
Guy McKhann, MD et al., "Clinical diagnosis of Alzheimer's disease: Report of the NINCDS-ADRDA Work Group under the auspices of Department of Health and Human Services Task Force on Alzheimer's Disease", Neurology vol. 34, Jul. 1984, pp. 939-944.
Z.P. Zhuang et al., "Radioiodinated Styrylbenzenes and Thioflavins as Probes for Amyloid Aggregates", J. Med. Chem., vol. 44, No. 12, 2001, pp. 1905-1914.
Masahiro Ono et al., "C-labeled stilbene derivatives as AB-aggregate-specific PET imaging agents for Alzheimer's disease", Elsevier, Nuclear Medicine and Biology, vol. 30, 2003, pp. 565-571.
Hank F. Kung et al., "Novel Stilbenes as Probes for Amyloid Plaques", J. Am. Chem. Soc., vol. 123, 2001, pp. 12740-12741.
Zhi-Ping Zhuang et al., "IBOX(2-(4'-dimethylaminophenyl)-6-iodobenzoxazole): a ligand for imaging amyloid plaques in the brain", Elsevier, Nuclear Medicine and Biology, vol. 28, 2001, pp. 887-894.
S. Furumoto et al., "[11C]BF-227: A New 11C-Labeled 2-Ethenylbenzoxazole Derivative for Amyloid-B Plagues Imaging", European Journal of Nuclear Medicine and Molecular Imaging, vol. 32, Sup. 1, 2005, p. 759.
Eric D. Agdeppa, PhD et al., "2-Dialkylamino-6-Acylmalononitrile Substituted Naphthalenes (DDNP Analogs): Novel Diagnostic and Therepeutic Tools in Alzheimer's Disease", Elsevier, Molecular Imaging and Biology, vol. 5, No. 6, 2004, pp. 404-417.
Zhi-Ping Zhuang et al., "Structure-Activity Relationship of Imidazo [1,2-a]pyridines as Ligands for Detecting B-Amyloid Plaques in the Brain", J. Med. chem. Volume 46, 2003, pp. 237-243.
William E. Klunk, MD et al., "Imaging Brain Amyloid in Alzheimer's Disease with Pittsburgh Compound-B", American Neurological Association, vol. 55, No. 3, Mar. 2004, pp. 306-319.
Nicolaas P.L.G. Verhoeff, MD et al., "In-Vivo Imaging of Alzheimer Disease B-Amyloid With [11C]SB-13 PET", American Journal of Geriatric Psychiatry, vol. 12:6, 2004, pp. 584-595.
Daniel M. Skovronsky et al., "In vivo detection of amyloid plaques in a mouse model of Alzeheimer's disease", Proc. National Academy Science, vol. 97, No. 13, Jun. 20, 2000, pp. 7609-7614.
Andrew B. Newberg et al., "Safety, Biodistricution, and Dosimetry of 123I-IMPY: A Novel Amyloid Plaque-Imaging Agent for the Diagnosis of Alzheimer's Disease", The Journal of Nuclear Medicine, vol. 47, No. 5, May 2006, pp. 748-754.
Young Soo Chang et al., "Synthesis and evaluation of benzothiophene derivatives as ligands for imaging B-amyloid plaques in Alzheimer's disease", Elsevier, Nuclear Medicine and Biology, vol. 33, 2006, pp. 811-820.
Lisheng Cai et al., "Synthesis and Evaluation of Two 18F-Labeled 6-Iodo-2-(4'-N,N-dimethylamino)phenylimidazo[1,2-a]pyridine Derivatives as Prospective Radioligands for B-Amyloid in Alzheimer's Disease", Journal of Medicinal Chemistry, vol. 47, No. 9, 2004, pp. 2208-2218.
Masahiro Ono et al., Benzofuran derivatives as AB-aggregate-specific imaging agents for Alzheimer's disease, Elsevier, Nuclear Medicine and Biology, vol. 29, 2002, pp. 633-642.
Maud Hervet et al. "Comparative Study on the Reactivity of 6-Haloimidazo[1,2-a]pyridine Derivatives towards Negishiand Stille-Coupling Reactions", Helvetica Chimica Acta, vol. 86, 2003, pp. 3461-3469.
Jerzy Lange et al., "A Structure-Activity Relationship Study of the Affinity of Selected Imidazo[1,2-a]Pyridine Derivatives, Congeners of Zolpidem, for the w1-Subtype of the Benzodiazepine Receptor" Acta Poloniae Pharamaceutica—Drug Research, vol. 58, No. 1, 2001, pp. 43-52.
Andrew Katsifis et al., "Synthesis of [123I}N',N'-Dimethyl-6-Methyl-(4'-lodophenyl)Imidazo[1,2-a]Pyridine-3-acetamide for the Study of Peripheral Benzodiazepine Receptors using SPECT", Journal of Labelled Compounds and Radiopharmaceuticals, vol. 43, 2000, pp. 385-394.
Gordon B. Barlin et al., "Imidazo[1,2-b]pyridazines, XX*T Syntheses of Some 3-Acylaminomethyl-6-(chloro, fluoro, methoxy, methylthio, phenoxy and phenylthio)-2-(phenyl, 4-t-butylphenyl, 4-cyclohexlphenyl, B-naphthyl and styryl)imidazo[1,2-b]pyridazines and Their Interaction with Central and Peripheral-Type Benzodiazepine Receptors", Australian Journal of Chemistry, vol. 49, No. 4, 1996, pp. 451-461.
A. Katsifis et al., "Synthesis of [123I]iodine labelled imidazo[1,2-b] pyridazines as potential probes for the study of peripheral benzodiazepine receptors using SPECT", Radiochim Acta, vol. 92, 2004, pp. 305-309.
Gordon B. Barlin, "Imidazo[1,2-b]pyridazines: Syntheses and Interaction with Central and Peripheral-Type (Mitochondrial) Benzodiazepine Receptors", J. Heterocyclic Chem., vol. 35, Sep.-Oct. 1998, pp. 1205-1217.
Danqian Xu et al., Short Paper, "Synthesis of 2-arylimidazo[1,2-a]pyrimidines by the Chichibabin synthesis in ionic liquids", J. Chem, Research (S), 2003, pp. 645-647.
Sundberg et al., "Preparation of 2-Aryl and 2-Aryloxymethyl Imidazo[1, 2-a]pyridines and Related Compounds", Journal of Heterocyclic Chemistry, vol. 25, No. 1, 1988, pp. 129-137.
Enguehard et al. J. Org. Chem., vol. 68, 2003, 4367-4370.
Chandra Shah et al. "Novel Human Histamine H3 Receptor Antagonist", Bioorganic & Medicinal Chemistry Letters, vol. 12, 2002, pp. 3309-3312.
Pauline J. Sanfilippo et al., "Synthesis of (Aryloxy)alkylamines. 2. Novel Imidazo-fused Heterocycles with Calcium Channel Blocking and Local Anesthetic Activity", Journal of Medicinal Chemistry, vol. 31, No. 11, 1988, pp. 2221-2227.
International Search Report dated Dec. 4, 2007, corresponding with International Application PCT/JP2007/071121.
Examination Report dated Sep. 27, 2011, corresponding against Australian Application 2007252658.
Chinese Second Office Action, dated Aug. 11, 2011, State Intellectual Property Office of the People's Republic of China, corresponding with Application No. 200780048027.6.
Office Action from State Intellectual Property Office of the Peoples of China, dated Mar. 19, 2012, corresponding in CN Patent Application 200780048027.6.
Office Action from State Intellectual Property Office of the Peoples of China, dated Mar. 26, 2012, corresponding in CN Patent Application 200780021402.8.
Patani et al., Bioisosterism: A Rational Approach in Drug Design, Chem. Rev. 96:3147-3176 (1996).
Office Action from State Intellectual Property Office of the Peoples Republic of China, dated Jan. 18, 2012, in CN appln. 200880121562.4.
Examination Report, Jan. 25, 2012, in NewZealand Appln. 577511.

\* cited by examiner

COMPOUND HAVING AFFINITY FOR AMYLOID

CROSS-REFERENCE TO RELATED APPLICATIONS

This is a U.S. National Phase of International Application PCT/JP2007/065955, filed Aug. 16, 2007, and claims foreign priority under 35 U.S.C. §119 based on Japanese Application No. 2006-324701, filed Nov. 30, 2006, the entire disclosures of which applications are hereby incorporated herein by reference.

TECHNICAL FIELD

The present invention relates to a compound for use in diagnosis of cerebral degenerative disease. More specifically, the invention relates to a compound useful for amyloid detection at lesion sites in diagnosis of Alzheimer's disease and other diseases with amyloid accumulation.

BACKGROUND ART

Diseases with the onset of deposition of a fibrous protein called amyloid in various organs or tissues in bodies are generally referred to as amyloidosis. A feature common to amyloidosis is that the fibrous protein called amyloid which is enriched with the β-sheet structure is deposited at various organs systemically or at sites topically so that functional abnormalities are triggered in the organs or tissues.

Alzheimer's disease (hereinafter referred to as AD), which is a typical amyloidosis disease, is known as a disease causing dementia. This disease is lethal with progressive deposition of amyloid in brain, and thus is said to be a disease that causes concern in society compared with other amyloidosis diseases. In recent years, the number of AD patients is rapidly increasing in developed countries with aging societies, thereby causing a social problem.

From the pathohistological viewpoint, AD is characterized by three pathological findings in brain, namely development of senile plaques, formation of neurofibrillary tangles, and extensive neuronal loss. The senile plaque has a structure mainly composed of amyloid, and is said to appear at the earliest stage of AD onset and thus is pathologically found in brain about 10 or more years before appearance of clinical symptoms.

AD is diagnosed by carrying out various evaluations of cognitive functions (for example, Hasegawa scale, ADAS-JCog and MMSE) in auxiliary combination with imaging diagnosis such as CT and MRI. However, the method based on such evaluations of cognitive functions is low in diagnostic sensitivity at the early stage of the onset, and is furthermore problematic in that diagnostic results are susceptible to inborn cognitive functions of individuals. At present, it is practically impossible to establish a definite diagnosis of AD while an AD patient is still alive, because the definite diagnosis requires a biopsy of a lesion (Non-Patent Document 1).

Meanwhile, a report tells that amyloid constituting senile plaques is an aggregate of amyloid β protein (hereinafter referred to as Aβ). Also, numerous reports tell that the Aβ aggregate forms a β-sheet structure that causes nerve cell toxicity. Based on these findings, the so-called "Amyloid Cascade Hypothesis" is proposed, which suggests that cerebral deposition of Aβ triggers the downstream phenomena, namely, formation of neurofibrillary tangles and neuronal loss (Non-Patent Document 2).

Based on these facts, attempts have recently been made to detect AD in vivo using a compound having high affinity with amyloid as a marker.

Many of such probes for imaging diagnoses of cerebral amyloid are hydrophobic low-molecular weight compounds that are high in affinity with amyloid and high in cerebral transferability and are labeled with various radioactive species such as $^{11}C$, $^{18}F$ and $^{123}I$. For example, reports tell $^{11}C$ or radioactive halogen labeled forms of compounds including various thioflavin derivatives such as 6-iodo-2-[4'-(N,N-dimethylamino)phenyl]benzothiazole (hereinafter referred to as TZDM) and 6-hydroxy-2-[4'-(N-methylamino)phenyl]benzothiazole (hereinafter referred to as 6-OH-BTA-1) (Patent Document 1, Non-Patent Document 3); stilbene compounds such as (E)-4-methylamino-4'-hydroxystilbene (hereinafter referred to as SB-13) and (E)-4-dimethylamino-4'-iodostilbene (hereinafter referred to as m-I-SB) (Patent Document 2, Non-Patent Document 4, Non-Patent Document 5); benzoxazole derivatives such as 6-iodo-2-[4'-(N,N-dimethylamino)phenyl]benzoxazole (hereinafter referred to as IBOX) and 6-[2-(fluoro)ethoxy]-2-[2-(2-dimethylaminothiazol-5-yl)ethenyl]benzoxazole (Non-Patent Document 6, Non-Patent Document 7), DDNP derivatives such as 2-(1-{6-[(2-fluoroethyl)(methyl)amino]-2-naphthyl}ethylidene)malononitrile (hereinafter referred to as FDDNP) (Patent Document 4, Non-Patent Document 8); and imidazopyridine derivatives such as 6-iodo-2-[4'-(N,N-dimethylamino)phenyl]imidazo[1,2-a]pyridine (hereinafter referred to as IMPY) (Patent Document 3, Non-Patent Document 9). Further, some of these probes for imaging diagnosis have been studied on human imaging and have been reported to show a significant accumulation in AD patient's brain compared with normal persons (Non-Patent Document 10, Non-Patent Document 11, Non-Patent Document 12, Non-Patent Document 13).

International Publication No. WO2007/002540 pamphlet discloses a series of compounds with a group having affinity with amyloid, to which a radioisotope labeling site is attached via ethylene glycol or polyethylene glycol (Patent Document 5).

International Publication No. WO2007/063946 pamphlet discloses a series of compounds to which a five-membered aromatic heterocyclic group is attached in order to prevent them from being metabolized in brain.

[Patent Document 1] JP-T-2004-506723
[Patent Document 2] JP-T-2005-504055
[Patent Document 3] JP-T-2005-512945
[Patent Document 4] JP-T-2002-523383
[Patent Document 5] International Publication No. WO2007/002540 pamphlet
[Patent Document 6] International Publication No. WO2007/063946 pamphlet
[Non-Patent Document 1] J. A. Hardy & G. A. Higgins, "Alzheimer's Disease: The Amyloid Cascade Hypothesis.", Science, 1992, 256, p. 184-185
[Non-Patent Document 2] G. McKhann et al., "Clinical diagnosis of Alzheimer's disease: Report of the NINCDS-ADRDA Work Group under the auspices of Department of Health and Human Services Task Force on Alzheimer's Disease.", Neurology, 1984, 34, p. 939-944
[Non-Patent Document 3] Z.-P. Zhuang et al., "Radioiodinated Styrylbenzenes and Thioflavins as Probes for Amyloid Aggregates.", J. Med. Chem., 2001, 44, p. 1905-1914
[Non-Patent Document 4] Masahiro Ono et al., "11C-labeled stilbene derivatives as Aβ-aggregate-specific PET imaging agents for Alzheimer's disease.", Nuclear Medicine and Biology, 2003, 30, p. 565-571

[Non-Patent Document 5] H. F. Kung et al., "Novel Stilbenes as Probes for amyloid plaques." J. American Chemical Society, 2001, 123, p. 12740-12741

[Non-Patent Document 6] Zhi-Ping Zhuang et al., "IBOX (2-(4'-dimethylaminophenyl)-6-iodobensoxazole): a ligand for imaging amyloid plaques in the brain.", Nuclear Medicine and Biology, 2001, 28, p. 887-894

[Non-Patent Document 7] Furumoto Y et al., "[$^{11}$C]BF-227: A New $^{11}$C-Labeled 2-Ethenylbenzoxazole Derivative for Amyloid-β Plaques Imaging." European Journal of Nuclear Medicine and Molecular Imaging, 2005, 32, Sup. 1, P 759

[Non-Patent Document 8] Eric D. Agdeppa et al., "2-Dialkylamino-6-Acylmalononitrile Substituted Naphthalenes (DDNP Analogs): Novel Diagnostic and Therapeutic Tools in Alzheimer's Disease.", Molecular Imaging and Biology, 2003, 5, p. 404-417

[Non-Patent Document 9] Zhi-Ping Zhuang et al., "Structure-Activity Relationship of Imidazo[1,2-a]pyridines as Ligands for Detecting βAmyloid Plaques in the Brain.", J. Med. Chem., 2003, 46, p. 237-243

[Non-Patent Document 10] W. E. Klunk et al., "Imaging brain amyloid in Alzheimer's disease with Pittsburgh Compound-B." Ann. Neurol., 2004, 55, p. 306-319

[Non-Patent Document 11] Nicolaas P. L. G. Verhoeff et al., "In-Vivo Imaging of Alzheimer Disease β-Amyloid With [11C]SB-13 PET.", American Journal of Geriatric Psychiatry, 2004, 12, p. 584-595

[Non-Patent Document 12] Hiroyuki Arai et al., "[11C]-BF-227 AND PET to Visualize Amyloid in Alzheimer's Disease Patients", Alzheimer's & Dementia: The Journal of the Alzheimer's Association, 2006, 2, Sup. 1, S312

[Non-Patent Document 13] Christopher M. Clark et al., "Imaging Amyloid with I123 IMPY SPECT", Alzheimer's & Dementia: The Journal of the Alzheimer's Association, 2006, 2, Sup. 1, S342

DISCLOSURE OF THE INVENTION

Problems to be Solved by the Invention

As described above, various compounds are disclosed as probes for imaging diagnosis for amyloid, and researched for clinical application.

Experiments in normal mice show that [$^{125}$I]-labeled TZDM, IBOX and m-I-SB are all transferred into brain 2 minutes after administration. However, these compounds are insufficient in clearance from normal tissues, and tend to accumulate gradually in brain as time passes after administration (JP-T-2005-512945; Zhi-Ping Zhuang et al., Nuclear Medicine and Biology, 2001, 28, p. 887-894; H. F. Kung et al., J. Am. Chem. Soc., 2001, 123, p. 12740-12741). When the clearance from normal tissues is insufficient, a problem arises in that sufficient contrast cannot be obtained at amyloid accumulation sites. [$^{11}$C]-labeled SB-13 shows a clearance from normal tissues in experiments in rats, however, it cannot be said that the clearance is sufficiently fast (Masahiro Ono et al., Nuclear Medicine and Biology, 2003, 30, p. 565-571).

Meanwhile, it is revealed that compounds having an imidazopyridine skeleton such as IMPY have a property of transferring to brain and accumulating at amyloid after administration, and also have an excellent property of rapid clearance from normal tissues unlike the above-described compounds, as a result of experiments using [$^{125}$I]-labeled compounds. However, IMPY is a compound positive in reverse mutation test. In order to use this compound as a probe for imaging diagnosis, sufficient care must be taken about dosage and administration manner (International Publication No. WO03/106439 pamphlet).

FDDNP is also reported to be positive in reverse mutation test. (International Publication No. WO03/106439 pamphlet)

A preferable probe targeting amyloid for imaging diagnosis would be a compound that is excellent in affinity with amyloid and sufficiently rapid in clearance from normal tissues like IMPY but is suppressed in toxicity such as mutagenicity. However, no compound with such properties has been disclosed.

Furthermore, in accordance with results of our studies (refers to Comparative Example 6 described later), it has been confirmed that IMPY accumulates unspecifically on white matter or other sites where amyloid is not deposited. As an AD diagnostic agent, a compound must be used which is suppressed in unspecific accumulation on sites other than amyloid deposition, but such a compound has not been disclosed.

The present invention has been made under such circumstances where various compounds have been disclosed as probes targeting amyloid for imaging diagnosis, but there has been no compound which is confirmed to have a clinically tolerable property, and aims at providing a compound that is effective as a probe targeting amyloid for imaging diagnosis and a diagnostic agent for Alzheimer's disease comprising the compound.

Means for Solving the Problems

The inventors have found that a group of compounds satisfying the above-described requirements can be obtained by using a compound with an imidazopyridine-phenyl skeleton or a skeleton similar thereto whose phenyl group has a carbon atom to which an oxygen atom is attached, and thus have completed the present invention.

Specifically, according to one aspect of the present invention, a compound represented by the following formula (1):

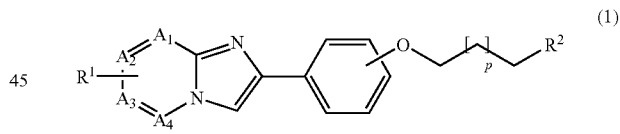

or a salt thereof, and a diagnostic agent for Alzheimer's disease comprising a compound represented by the above formula (1) or a salt thereof are provided. Specifically, a compound represented by the above formula (1) or a salt thereof provides a highly-specific diagnostic agent for Alzheimer's disease. A highly-specific diagnostic agent for Alzheimer's disease here refers to a diagnostic agent which has a property of accumulating at amyloid and hardly accumulating at other sites or rapidly clearing other sites even if it accumulates there, and thus shows high specificity of amyloid imaging in a certain period of time after administration.

In the formula (1), $A_1$, $A_2$, $A_3$ and $A_4$ independently represent a carbon or nitrogen, and it is necessary that at least one of these represents a carbon. Preferably, 3 or more of $A_1$, $A_2$, $A_3$ and $A_4$ represent carbons, and more preferably, all of them represent carbons. In the formula (1), $R^1$ binds to a carbon represented by $A_1$, $A_2$, $A_3$ or $A_4$. A binding site for $R^1$ is preferably a carbon represented by $A_3$, that is, a carbon at 6-position.

According to the preferable embodiment of the present invention, a compound represented by the following formula (2):

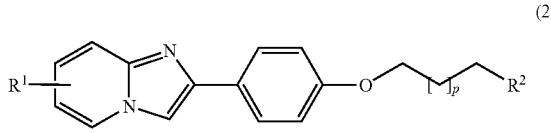

(2)

or a salt thereof, and a diagnostic agent for Alzheimer's disease comprising a compound represented by the above formula (1) or a salt thereof are provided.

In the formulas (1) and (2), $R^1$ is a radioactive halogen substituent. As $R^1$, can be used various radioactive halogens, preferably a radioactive halogen selected from the group consisting of $^{18}F$, $^{76}Br$, $^{123}I$, $^{124}I$, $^{125}I$ and $^{131}I$, and more preferably $^{18}F$ or $^{123}I$.

$R^2$ is a group selected from the group consisting of hydrogen, hydroxyl group, methoxy group, carboxyl group, amino group, N-methylamino group, N,N-dimethylamino group and cyano group. $R^2$ is preferably hydrogen, hydroxyl group, carboxyl group or amino group, more preferably hydrogen or hydroxyl group and particularly preferably hydroxyl group.

In addition, p is an integer of 0 to 2.

Therefore, according to the particularly preferable embodiment, a compound of the present invention is selected from the group consisting of 2-(4'-ethoxyphenyl)-6-[$^{123}$I]iodoimidazo[1,2-a]pyridine, 2-(4'-ethoxyphenyl)-6-[$^{125}$I]iodoimidazo[1,2-a]pyridine, 2-(4'-ethoxyphenyl)-6-[$^{131}$I]iodoimidazo[1,2-a]pyridine, 2-[4'-(2"-hydroxyethoxy)phenyl]-6-[$^{123}$I]iodoimidazo[1,2-a]pyridine, 2-[4'-(2"-hydroxyethoxy)phenyl]-6-[$^{125}$I]iodoimidazo[1,2-a]pyridine, 2-[4'-(2"-hydroxyethoxy)phenyl]-6-[$^{131}$I]iodoimidazo[1,2-a]pyridine, 2-[4'-(3"-hydroxypropoxy)phenyl]-6-[$^{123}$I]iodoimidazo[1,2-a]pyridine, 2-[4'-(3"-hydroxypropoxy)phenyl]-6-[$^{125}$I]iodoimidazo[1,2-a]pyridine, 2-[4'-(3"-hydroxypropoxy)phenyl]-6-[$^{131}$I]iodoimidazo[1,2-a]pyridine, 2-(4'-ethoxyphenyl)-6-[$^{123}$I]iodoimidazo[1,2-a]pyridine, 2-(4'-ethoxyphenyl)-6-[$^{125}$I]iodoimidazo[1,2-a]pyridine, 2-(4'-ethoxyphenyl)-6-[$^{131}$I]iodoimidazo[1,2-a]pyridine, 2-[3'-(2"-hydroxyethoxy)phenyl]-6-[$^{123}$I]iodoimidazo[1,2-a]pyridine, 2-[3'-(2"-hydroxyethoxy)phenyl]-6-[$^{125}$I]iodoimidazo[1,2-a]pyridine, 2-[3'-(2"-hydroxyethoxy)phenyl]-6-[$^{131}$I]iodoimidazo[1,2-a]pyridine, 2-[3'-(3"-hydroxypropoxy)phenyl]-6-[$^{123}$I]iodoimidazo[1,2-a]pyridine, 2-[3'-(3"-hydroxypropoxy)phenyl]-6-[$^{125}$I]iodoimidazo[1,2-a]pyridine and 2-[3'-(3"-hydroxypropoxy)phenyl]-6-[$^{131}$I]iodoimidazo[1,2-a]pyridine, and a diagnostic agent for Alzheimer's disease of the present invention is a diagnostic agent for Alzheimer's disease comprising an above-mentioned compound or a salt thereof.

According to another aspect of the present invention, a compound represented by the following formula (3):

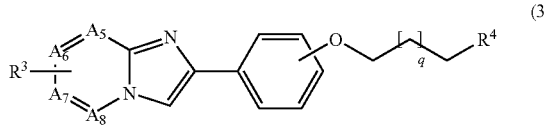

(3)

or a salt thereof is provided.

In the formula (3), $A_5$, $A_6$, $A_7$ and $A_8$ independently represent a carbon or nitrogen, and it is necessary that at least one of these represents a carbon. Preferably, 3 or more of $A_5$, $A_6$, $A_7$ and $A_8$ represent carbons, and more preferably, all of them represent carbons. In the formula (3), $R^3$ binds to a carbon represented by $A_5$, $A_6$, $A_7$ or $A_8$. A binding site for $R^3$ is preferably a carbon represented by $A_7$ that is, a carbon at 6-position.

According to the preferable embodiment of the present invention, a compound represented by the following formula (4):

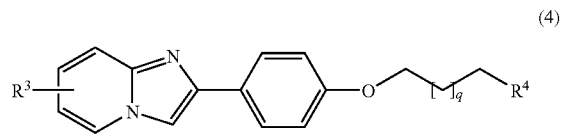

(4)

is provided.

In the formulas (3) and (4), $R^3$ is a group selected from the group consisting of a non-radioactive halogen substituent, nitro group, trialkylammonium group having alkyl chains with 1 to 4 carbon atoms, trialkylstannyl substituent having alkyl chains with 1 to 4 carbon atoms and triphenylstannyl group. As a non-radioactive halogen substituent, a halogen capable of being a target of nucleophilic substitution reactions using a radioactive fluorine or a halogen capable of being a target of isotope exchange reactions with a radioactive iodine can be used, and preferably chlorine, iodine or bromine can be used. As a trialkylstannyl substituent, various substituents can be used, and trimethylstannyl substituent and tributylstannyl substituent are preferably used.

$R^4$ is a group selected from the group consisting of hydrogen, hydroxyl group, methoxy group, carboxyl group, amino group, N-methylamino group, N,N-dimethylamino group and cyano group. $R^2$ is preferably hydrogen, hydroxyl group, carboxyl group or amino group, more preferably hydrogen or hydroxyl group and particularly preferably hydroxyl group.

In addition, q is an integer of 0 to 2.

Effects of the Invention

The present invention provides a novel compound and a diagnostic agent for Alzheimer's disease, which have affinity with amyloid and have an excellent capability of imaging amyloid in a living body.

BEST MODE FOR CARRYING OUT THE INVENTION

A Method for Synthesis of a Precursor Compound for a Radioactive Halogen-Labeled Compound Hereinafter, a method for synthesis of a precursor compound for a radioactive halogen-labeled compound according to an embodiment of the present invention will be described, taking the case of 6-tributylstannyl-2-[4'-(2"-hydroxyethoxy)phenyl]imidazo[1,2-a]pyridine as an example.

For the synthesis of 6-tributylstannyl-2-[4'-(2"-hydroxyethoxy)phenyl]imidazo[1,2-a]pyridine, first, 4'-hydroxyacetophenone is allowed to react with cupric bromide to prepare 2-bromo-4'-hydroxyacetophenone (FIG. 1, Step 1). In this instance, the reaction can be conducted in accordance with ordinary methods, for example, the method described in a literature, King, L. Carroll & Ostrum, G. Kenneth, Journal of Organic Chemistry, 1964, 29(12), p. 3459-3461.

Then, 2-bromo-4'-hydroxyacetophenone as prepared above is allowed to react with 2-amino-5-iodopyridine to prepare 2-(4'-hydroxyphenyl)-6-iodoimidazo[1,2-a]pyridine (FIG. 1, Step 2). This step can be done according to the following procedure.

First, 2-bromo-4'-hydroxyacetophenone and 2-amino-5-iodopyridine are dissolved in an inactive solvent such as acetonitrile, and are allowed to react with each other at a reflux temperature for 2 to 6 hours to produce 2-(4'-hydroxyphenyl)-6-iodoimidazo[1,2-a]pyridine hydrobromide salt as white precipitates. The solvent used in this instance may be acetonitrile or another solvent that is usually employed in a similar reaction, for example, methanol and acetone. The reaction temperature may be a temperature allowing refluxing, for example, 110° C. when the solvent is acetonitrile. The amount of the solvent to be used may be an amount sufficient to effect the reaction, however, it should be noted that if the solvent is too much, it will become difficult to obtain precipitates of reaction products. For example, when 2-bromo-4'-hydroxyacetophenone in an amount corresponding to 10 mmol is used for the reaction, the amount of a solvent to be used can be about 40 to 80 mL.

Next, the reaction solution is filtered to recover the precipitates. The white precipitates are suspended in a mixed solution of methanol/water (1:1). Then, an aqueous saturated solution of sodium hydrogencarbonate is added thereto in a very excessive amount relative to the suspended precipitates to release 2-(4'-hydroxyphenyl)-6-iodoimidazo[1,2-a]pyridine as precipitates. The newly generated precipitates are filtered to recover 2-(4'-hydroxyphenyl)-6-iodoimidazo[1,2-a]pyridine as the target compound in this step (FIG. 1, Step 2). The amount of the mixed solution of methanol/water is not specifically limited as long as it is sufficient to effect the reaction. However, it should be noted that if the amount of the mixed solution is too much, precipitation of products will be hindered. For example, when 2-bromo-4'-hydroxyacetophenone in an amount corresponding to 10 mmol is used, the mixed solution of methanol/water may be used in an amount of about 40 to 100 mL. The amount of sodium hydrogencarbonate is not specifically limited as long as it is very excessive relative to the above-described precipitates as reaction substrates. For example, when the reaction is effected under the above-described conditions, the amount of an aqueous saturated solution of sodium hydrogencarbonate to be added to the reaction solution can be about 50 mL.

Here, 2-bromoethanol and t-butyldiphenylchlorosilane (TBDPSCl) are reacted with each other to prepare 1-bromo-2-(t-butyldiphenylsiloxy)ethane (FIG. 1, Step 3), separately. In this instance, the reaction can be carried out in accordance with ordinary methods, for example, the method described in a literature (Organic Syntheses, Coll. Vol. 10, p. 170 (2004); Vol. 79, p. 59 (2002)).

Then, the 2-(4'-hydroxyphenyl)-6-iodoimidazo[1,2-a]pyridine prepared above is sufficiently dried, dissolved in N,N-dimethylformamide, and potassium carbonate and 1-bromo-2-(t-butyldiphenylsiloxy)ethane were added thereto. After this mixture was stirred at about 90° C. for about 2 hours, a saturated sodium chloride solution is added followed by extraction with ethyl acetate, and the ethyl acetate layer is concentrated and subjected to chromatogram purification to obtain 2-[4'-(2''-t-butyldiphenylsiloxyethoxy)phenyl]-6-iodoimidazo[1,2-a]pyridine (FIG. 1, Step 4). The amount of potassium carbonate may be an amount that can neutralize hydrobromic acid generated from 1-bromo-2-(t-butyldiphenylsiloxy)ethane during the reaction, and is typically about double to triple the other reactant 1-bromo-2-(t-butyldiphenylsiloxy)ethane in molar ratio. Further, the 1-bromo-2-(t-butyldiphenylsiloxy)ethane can be used in an excessive amount relative to the reaction substrate, and is typically about 1.5 times the reaction substrate 2-(4'-hydroxyphenyl)-6-iodoimidazo[1,2-a]pyridine in molar ratio.

Then, t-butyldiphenylsilyl group of the obtained 2-[4'-(2''-t-butyldiphenylsiloxyethoxy)phenyl]-6-iodoimidazo[1,2-a]pyridine is deprotected using tetrabutylammonium fluoride to obtain 2-[4'-(2''-hydroxyethoxy)phenyl]-6-iodoimidazo[1,2-a]pyridine (FIG. 1, Step 5). In this instance, the reaction can be carried out in accordance with ordinary methods, for example, the method described in a literature (Organic Syntheses, Coll. Vol. 9, p. 417 (1998); Vol. 74, p. 248 (1997)).

The obtained 2-[4'-(2''-hydroxyethoxy)]phenyl]-6-iodoimidazo[1,2-a]pyridine is dissolved in dioxane, and triethylamine is added to the solution, followed by addition of bis(tributyltin) and a catalytic amount of tetrakis-triphenylphosphine palladium. This reaction solution is heated at about 90° C. to effect reaction for about 24 hours, and then a solvent is distilled off and chromatographic purification is performed to obtain 6-tributylstannyl-2-[4'-(2''-hydroxyethoxy)phenyl]imidazo[1,2-a]pyridine as the target compound (FIG. 2, Step 1). The amount of bis(tributyltin) to be used in this instance may be an amount satisfying a condition where it is excessive relative to the reaction substrate, specifically, it is about 1.5 times in molar ratio relative to the reaction substrate 2-[4'-(2''-hydroxyethoxy)phenyl]-6-iodoimidazo[1,2-a]pyridine.

When a compound with a substituent at the 6-position in the imidazo pyridine ring being a trialkylstannyl substituent other than the tributylstannyl substituent is obtained, various bis(trialkyltin)s that fit purposes can be used instead of bis(tributyltin) in FIG. 2, Step 1. For example, when a compound having a trimethylstannyl substituent as a substituent at the 6-position is synthesized, a reaction similar to the above can be performed using bis(trimethyltin) in FIG. 2, Step 1.

A compound with an imidazopyridine ring in which the binding site for the functional group is a carbon atom other than the carbon at 6-position can be obtained by using a compound with a pyridine ring to which iodine is bonded at a different site instead of 2-amino-5-iodopyridine in FIG. 1, Step 2. For example, when a binding site for the functional group is the carbon at 8-position in the imidazopyridine ring, 2-amino-3-iodopyridine may be used instead of 2-amino-5-iodopyridine in FIG. 1, Step 2.

(A Method for Synthesis of a Radioactive Halogen-Labeled Compound)

Next, a method for production of a radioactive halogen-labeled compound according to another aspect of the present invention will be described, taking the case of radioactive iodine-labeled compounds as an example.

The synthesis of radioactive iodine-labeled compounds can be performed by dissolving the labeling precursor compound prepared as above procedure in an inert organic solvent, adding thereto a [$^{123}$I]sodium iodide solution or the like obtained by known methods, and adding thereto an acid and an oxidizing agent. As an inert organic solvent dissolving the labeling precursor compound, various solvents having no reactivity with the labeling precursor, [$^{123}$I]sodium iodide and the like can be used, and preferably methanol can be used.

As the acid, may be used various ones, and preferably hydrochloric acid.

The oxidizing agent is not particularly limited as long as it can effect the oxidation of iodine in the reaction solution, and is preferably hydrogen peroxide or peracetic acid. The amount of the oxidizing agent to be added may be an amount sufficient to oxidize iodine in the reaction solution.

A compound labeled with a radioactive halogen other than iodine can be synthesized by labeling a labeling precursor that fits a purpose of synthesis with a radioactive halogen that fits the purpose. For example, in order to synthesize 6-[$^{18}$F]fluoro-2-[4'-(2''-hydroxyethoxy)phenyl]imidazo[1,2-a]pyridine, the labeling precursor 2-[4'-(2''-hydroxyethoxy)phenyl]-6-nitroimidazo[1,2-a]pyridine can be reacted with [$^{18}$F]fluoride ion in the presence of a phase transfer catalyst and potassium carbonate.

(Methods for Preparing and Using a Diagnostic Agent in Accordance with the Present Invention)

The diagnostic agent according to the present invention can be prepared as a solution which comprises the present radioactive halogen-labeled compound blended in water, a physiological saline solution or a Ringer's solution optionally adjusted to an appropriate pH, like other commonly-known radioactive diagnostic agents. In this instance, concentration of the present compound should be adjusted to not more than the concentration at which stability of the present compound is ensured. Dosage of the present compound is not specifically limited as long as it is sufficient to obtain an image of distribution of an administered agent. For example, in case of iodine-123($^{123}$I)-labeled compounds and fluorine-18($^{18}$F)-labeled compounds, about 50 to 600 MBq per adult body of 60 kg weight can be administered intravenously or locally. Distribution of administered agents can be imaged by known methods. For example, iodine-123 ($^{123}$I)-labeled compounds can be imaged by a SPECT apparatus while fluorine-18 ($^{18}$F)-labeled compounds can be imaged by a PET apparatus.

EXAMPLE

Hereinafter, the present invention is described below in more detail by way of Examples, Comparative Examples and Reference Examples. However, these Examples never limit the scope of the present invention.

In the following Examples, the names of the individual compounds used in the experiment are defined as shown in Table 1.

TABLE 1

| Compound name | Common name |
| --- | --- |
| Compound 1 | 2-[4'-(2''-hydroxyethoxy)phenyl]-6-[$^{123}$I]iodoimidazo[1,2-a]pyridine |
| Compound 2 | 2-(4'-ethoxyphenyl)-6-[$^{123}$I]iodoimidazo[1,2-a]pyridine |
| Compound 3 | 2-[4'-(2''-hydroxyethoxy)phenyl]-6-iodoimidazo[1,2-a]pyridine |
| Compound 4 | 2-[3'-(2''-hydroxyethoxy)phenyl]-6-[$^{123}$I]iodoimidazo[1,2-a]pyridine |
| Compound 5 | 2-[3'-(2''-hydroxyethoxy)phenyl]-6-iodoimidazo[1,2-a]pyridine |
| Compound 6 | 2-[4'-(3''-hydroxypropoxy)phenyl]-6-[$^{123}$I]iodoimidazo[1,2-a]pyridine |
| Compound 7 | 2-[4'-(3''-hydroxypropoxy)phenyl]-6-iodoimidazo[1,2-a]pyridine |
| Compound 8 | 2-(4'-ethoxyphenyl)-6-iodoimidazo[1,2-a]pyridine |

Example 1

Synthesis of 2-[4'-(2''-hydroxyethoxy)phenyl]-6-iodoimidazo[1,2-a]pyridine (Non-Radioactive Iodinated Form)

50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was heated under reflux. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 1, Step 1).

441 mg (corresponding to 2.0 mmol) of 2-bromo-4'-hydroxyacetophenone and 449 mg (corresponding to 2.0 mmol) of 2-amino-5-iodopyridine were dissolved in 15 mL of acetonitrile. The resulting solution was heated under reflux in an oil bath at 110° C. for 5 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 10 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 526 mg (corresponding to 1.56 mmol) of 2-(4'-hydroxyphenyl)-6-iodoimidazo[1,2-a]pyridine (FIG. 1, Step 2).

Separately, 2.50 g (corresponding to 20.0 mmol) of 2-bromoethanol and 2.72 g (corresponding to 40.0 mmol) of imidazole were dissolved in 10 mL of dimethylformamide (DMF), and cooled to 0° C. Then, 5.50 g (corresponding to 20.0 mmol) of t-butyldiphenylchlorosilane (TBDPSCl) was added thereto. After the reaction mixture was stirred at room temperature for 18 hours, a saturated sodium chloride aqueous solution was added, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=10/1) to obtain 7.04 g (corresponding to 19.4 mmol) of 1-bromo-2-(t-butyldiphenylsiloxy)ethane (FIG. 1, Step 3).

200 mg (corresponding to 0.595 mmol) of 2-(4'-hydroxyphenyl)-6-iodoimidazo[1,2-a]pyridine was dissolved in 3.0 mL of dimethylformamide, and 247 mg (corresponding to 1.79 mmol) of potassium carbonate was added thereto. Then, 259 mg (corresponding to 0.714 mmol) of 1-bromo-2-(t-butyldiphenylsiloxy)ethane was added thereto. After the reaction mixture was stirred at 90° C. for 2 hours, a saturated sodium chloride aqueous solution was added, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=2/1) to obtain 368 mg (corresponding to 0.595 mmol) of 2-[4'-(2''-t-butyldiphenylsiloxyethoxy)phenyl]-6-iodoimidazo[1,2-a]pyridine (FIG. 1, Step 4).

368 mg (corresponding to 0.595 mmol) of 2-[4'-(2''-t-butyldiphenylsiloxyethoxy)phenyl]-6-iodoimidazo[1,2-a]pyridine was dissolved in 1.0 mL of tetrahydrofuran (THF), and 0.70 mL of a 1.0 mol/L solution in tetrahydrofuran of tetrabutylammoniumfluoride (TBAF) was added thereto. After the reaction mixture was stirred at room temperature for 2 hours, ammonium chloride aqueous solution was added, followed by addition of 5.0 mL of water and 2.0 mL of acetonitrile. Then precipitates were filtered. The filtered precipitates were washed with water and acetonitrile in this order, to obtain 226 mg (corresponding to 0.595 mmol) of 2-[4'-(2"-hydroxyethoxy)phenyl]-6-iodoimidazo[1,2-a]pyridine (FIG. 1, Step 5).

The NMR measurement results of the resulting 2-[4'-(2"-hydroxyethoxy)phenyl]-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: dimethylsulfoxide-d6; resonance frequency: 500 MHz): δ 8.95 (s, 1H), 8.27 (s, 1H), 7.87 (d, J=8.7 Hz, 2H), 7.54-7.46 (m, 2H), 7.04 (d, J=8.7 Hz, 2H), 4.04 (t, J=4.6 Hz, 2H), 3.73 (t, J=4.6 Hz, 2H).

$^{13}$C-NMR (solvent: dimethylsulfoxide-d6, resonance frequency: 500 MHz): δ 158.9, 143.0, 142.4, 133.5, 131.5, 127.1, 124.4, 116.7, 114.8, 108.1, 76.7, 69.5, 59.4.

Example 2

Synthesis of 6-tributylstannyl-2-[4'-(2"-hydroxyethoxy)phenyl]-imidazo[1,2-a]pyridine 100 mg (corresponding to 0.263 mmol) of 2-[4'-(2"-hydroxyethoxy)phenyl]-6-iodoimidazo[1,2-a]pyridine obtained in Example 1 was dissolved in 4.0 mL of dioxane, and 2.0 mL of triethylamine was added thereto. Then, 0.20 mL (corresponding to 0.39 mmol) of bis(tributyltin) and 20.1 mg (a catalytic amount) of tetrakis-triphenylphosphine palladium were added thereto. After the reaction mixture was stirred at 90° C. for 21 hours, the solvent was distilled off under reduced pressure. The residue was purified by flash silica gel column chromatography (elution solvent: hexane/ethyl acetate=1/2), to obtain 75.3 mg (corresponding to 0.139 mmol) of 6-tributylstannyl-2-[4'-(2"-hydroxyethoxy)phenyl]imidazo[1,2-a]pyridine (FIG. 2, Step 1).

The NMR measurement results of the resulting 6-tributylstannyl-2-[4'-(2"-hydroxyethoxy)phenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl; resonance frequency: 500 MHz): δ 7.98 (s, 1H), 7.89 (d, J=8.7 Hz, 1H), 7.75 (s, 1H), 7.56 (d, J=8.7 Hz, 1H), 7.15 (d, J=8.7 Hz, 1H), 6.98 (d, J=8.7 Hz, 1H), 4.13 (t, J=4.6 Hz, 2H), 3.99 (t, J=4.6 Hz, 2H), 2.63 (s, 3H), 1.64-1.51 (m, 6H), 1.36 (sextet, J=7.3 Hz, 6H), 1.19-1.06 (m, 6H), 0.92 (t, J=7.3 Hz, 9H).

$^{13}$C-NMR (solvent: chloroform-dl, resonance frequency: 500 MHz): δ 158.6, 145.7, 145.0, 131.2, 130.0, 127.4, 127.2, 121.9, 116.9, 114.8, 106.4, 69.3, 61.4, 29.0, 27.3, 13.7, 9.8.

Example 3

Synthesis of 2-[4'-(2"-hydroxyethoxy)phenyl]-6-[$^{123}$I]iodoimidazo[1,2-a]pyridine To 60 µL of a solution of 6-tributylstannyl-2-[4'-(2"-hydroxyethoxy)phenyl]imidazo[1,2-a]pyridine (concentration: 1 mg/mL) in a mixed solution of methanol/dimethylsulfoxide (mixing ratio: 9/1), 150 µL of 1 mol/L hydrochloric acid, 15 µL of 1 mmol/L sodium iodide, 250 µL of [$^{123}$I]sodium iodide of 274 MBq and 15 µL of 10% (w/v) hydrogen peroxide were added. After the mixed solution was left to stand at 50° C. for 10 minutes, it was subjected to HPLC under the following conditions, to obtain a fraction of 2-[4'-(2"-hydroxyethoxy)phenyl]-6-[$^{123}$I]iodoimidazo[1,2-a]pyridine.

HPLC Conditions:
Column: Phenomenex Luna C18 (trade name; manufactured by Phenomenex Co.; size: 4.6×150 mm)
Mobile phase: 0.1% trifluoroacetic acid in water/0.1% trifluoroacetic acid in acetonitrile=80/20 to 0/100 (17 minutes)
Flow rate: 1.0 mL/min.
Detector: Ultraviolet visible absorptiometer (Detection wavelength: 282 nm) and radioactivity counter (manufactured by raytest: type STEFFI)

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-[4'-(2"-hydroxyethoxy)phenyl]-6-[$^{123}$I]iodoimidazo[1,2-a]pyridine. The column was rinsed with 1 mL of water, and then 1 mL of diethyl ether was passed therethrough to elute 2-[4'-(2"-hydroxyethoxy)phenyl]-6-[$^{123}$I]iodoimidazo[1,2-a]pyridine. The amount of radioactivity of the obtained compound was 22 MBq at the end of synthesis. Further, the TLC analysis was conducted under the following conditions, and as a result, the radiochemical purity of the compound was 97%.

TLC Analysis Conditions:
TLC plate: Silica Gel 60 $F_{254}$ (trade name; manufactured by Merck & Co., Inc.)
Mobile phase: Chloroform/methanol/triethylamine=100/1/2
Detector: Rita Star (trade name; manufactured by raytest)

Example 4

Synthesis of 2-(4'-ethoxyphenyl)-6-iodoimidazo[1,2-a]pyridine (Non-Radioactive Iodinated Form)

30 mL of ethyl acetate was added to 2.72 g (corresponding to 12.2 mmol) of cupric bromide to obtain a suspension, to which 1.00 g (corresponding to 6.09 mmol) of 4'-ethoxyacetophenone was added. Then, the mixture was heated under reflux. After 3 hours, the reaction mixture was cooled down to room temperature and filtered. Then, the resulting filtrate was concentrated under reduced pressure. The residue was dissolved in ethyl acetate and concentrated. The resulting crude product was purified by silica gel column chromatography (elution solvent: hexane/ethyl acetate=10/1), to obtain 1.20 g (corresponding to 4.94 mmol) of 2-bromo-4'-ethoxyacetophenone (FIG. 3, Step 1).

1.20 g (corresponding to 4.94 mmol) of 2-bromo-4'-ethoxyacetophenone and 1.09 g (corresponding to 4.95 mmol) of 2-amino-5-iodopyridine were dissolved in 20 mL of acetonitrile. The resulting solution was heated under reflux in an oil bath at 110° C. for 1.5 hours. After the completion of the reaction, the reaction solution was cooled down to room temperature, and precipitates were filtered. Then, the precipitates were washed with acetonitrile and dried under reduced pressure. The resulting crude crystals were suspended in a mixed solution of 10 mL of water and 5 mL of methanol. Then, about 20 mL of a saturated sodium hydrogencarbonate solution was added thereto, and the mixture was sonicated for 10 minutes using an ultrasonic washing machine. Precipitates were filtered and recovered from the resulting mixture, sufficiently washed with water, and dried under reduced pressure, to obtain 1.64 g (corresponding to 4.50 mmol) of 2-(4'-ethoxyphenyl)-6-iodoimidazo[1,2-a]pyridine (FIG. 3, Step 2).

The NMR measurement results of the resulting 2-(4'-ethoxyphenyl)-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: dimethylsulfoxide-d6; resonance frequency: 500 MHz): δ 9.06 (s, 1H), 8.38 (s, 1H), 7.86 (d, J=8.7 Hz, 2H), 7.77-7.57 (m, 2H), 7.06 (d, J=8.7 Hz, 2H), 4.10 (q, J=6.9 Hz, 2H), 1.36 (t, J=6.9 Hz, 3H).

$^{13}$C-NMR (solvent: dimethylsulfoxide-d6, resonance frequency: 500 MHz): δ 159.3, 141.1, 140.3, 135.9, 132.0, 127.3, 122.1, 115.3, 114.9, 108.5, 78.6, 63.2, 14.5.

Example 5

Synthesis of 6-tributylstannyl-2-(4'-ethoxyphenyl) imidazo[1,2-a]pyridine 364 mg (corresponding to 1.00 mmol) of 2-(4'-ethoxyphenyl)-6-iodoimidazo[1,2-a]pyridine obtained in Example 4 was dissolved in 4.0 mL of dioxane, and 2 mL of triethylamine was added thereto. Then, 0.76 mL (corresponding to 1.5 mmol) of bis(tributyltin) and 76.3 mg (a catalytic amount) of tetrakis-triphenylphosphine palladium were added thereto. After the reaction mixture was stirred at 90° C. for 23 hours, the solvent was distilled off under reduced pressure. The residue was purified by flash silica gel column chromatography (elution solvent: hexane/ethyl acetate=5/1), to obtain 331 mg (corresponding to 0.628 mmol) of 6-tributylstannyl-2-(4'-ethoxyphenyl)imidazo[1,2-a]pyridine (FIG. 4, Step 1).

The NMR measurement results of the resulting 6-tributylstannyl-2-(4'-ethoxyphenyl)imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-di; resonance frequency: 500 MHz): δ 7.96 (s, 1H), 7.88 (d, J=8.7 Hz, 2H), 7.74 (s, 1H), 7.58 (d, J=8.7 Hz, 1H), 7.14 (d, J=8.7 Hz, 1H), 6.96 (d, J=8.7 Hz, 2H), 4.07 (q, J=6.9 Hz, 2H), 1.63-1.49 (m, 6H), 1.43 (t, J=6.9 Hz, 3H), 1.39-1.31 (m, 6H), 1.18-1.04 (m, 6H), 0.90 (t, J=7.3 Hz, 9H).

$^{13}$C-NMR (solvent: chloroform-dl, resonance frequency: 500 MHz): δ 159.0, 145.7, 145.2, 131.2, 130.1, 127.4, 126.7, 121.9, 117.0, 114.8, 106.4, 63.6, 29.1, 27.4, 15.0, 13.8, 9.9.

Example 6

Synthesis of 2-(4'-ethoxyphenyl)-6-[$^{123}$I]iodoimidazo[1,2-a]pyridine

To 60 μL of a solution of 6-tributylstannyl-2-(4'-ethoxyphenyl)imidazo[1,2-a]pyridine (concentration: 1 mg/mL) in a mixed solution of methanol/dimethylsulfoxide (mixing ratio: 9/1), 90 μL of 2 mol/L hydrochloric acid, 15 μL of 1 mmol/L sodium iodide, 100 μL of [$^{123}$I]sodium iodide of 436 MBq and 15 μL of 10% (w/v) hydrogen peroxide were added. After the mixed solution was left to stand at 50° C. for 10 minutes, it was subjected to HPLC under the following conditions to obtain a fraction of 2-(4'-ethoxyphenyl)-6-[$^{123}$I] iodoimidazo[1,2-a]pyridine.

HPLC Conditions:
Column: Phenomenex Luna C18 (trade name; manufactured by Phenomenex Co.; size: 4.6×150 mm)
Mobile phase: 0.1% trifluoroacetic acid in water/0.1% trifluoroacetic acid in acetonitrile=80/20 to 0/100 (17 minutes)
Flow rate: 1.0 mL/min.
Detector: Ultraviolet visible absorptiometer (Detection wavelength: 282 nm) and radioactivity counter (manufactured by raytest: type STEFFI)

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-(4'-ethoxyphenyl)-6-[$^{123}$I]iodoimidazo[1,2-a]pyridine. The column was rinsed with 1 mL of water, and then 1 mL of diethyl ether was passed therethrough to elute 2-(4'-ethoxyphenyl)-6-[$^{123}$I]iodoimidazo[1,2-a]pyridine. The amount of radioactivity of the obtained compound was 88 MBq at the end of synthesis. Further, the TLC analysis was conducted under the following conditions, and as a result, the radiochemical purity of the compound was 98%.

TLC Analysis Conditions:
TLC plate: Silica Gel 60 $F_{254}$ (trade name; manufactured by Merck & Co., Inc.)
Mobile phase: Chloroform/methanol/triethylamine=100/1/2
Detector: Rita Star (trade name; manufactured by raytest)

Reference Example 1

Synthesis of [$^{123}$I]-IMPY

[$^{123}$I]-IMPY was synthesized in accordance with the following steps for use in Comparative Examples for evaluations on measurement of log $P_{octanol}$ and accumulations in brain.

In accordance with the method described in a literature (Zhi-Ping Zhuang et al., J. Med. Chem., 2003, 46, p. 237-243), 6-tributylstannyl-2-[4'-(N,N-dimethylamino)phenyl] imidazo[1,2-a]pyridine was synthesized, and dissolved in methanol (concentration: 1 mg/mL). To 53 μL of the resulting solution, 75 μL of 1 mol/L hydrochloric acid, 60-70 μL of [$^{123}$I]sodium iodide of 224-253 MBq, 10 μL of a 1 mmol/L sodium iodide solution and 15 μL of 10% (w/v) hydrogen peroxide were added. After the mixed solution was left to stand at 50° C. for 10 minutes, the solution was subjected to HPLC under the same conditions as in Example 3, to obtain a fraction of [$^{123}$I]-IMPY.

10 ml of water was added to the fraction. The resulting solution was passed through a reversed phase column (trade name: Sep-Pak (registered trademark) Light C8 Cartridges manufactured by Waters; the packed amount of the packing agent: 145 mg), so that the column adsorbs and collects the [$^{123}$I]-IMPY. The column was rinsed with 1 mL of water, and then 1 mL of diethyl ether was passed therethrough, to elute [$^{123}$I]-IMPY. The obtained radioactivity was 41-57 MBq at the end of synthesis. Further, the TLC analysis was conducted under the same conditions as described in Example 3, and as a result, the radiochemical purity of the compound was 93%.

Example 7, Comparative Example 1 to 3

Measurement of Affinity with Amyloid

Affinity of the present compounds with amyloid was examined by the following in vitro binding tests.

(1) $Aβ_{1-42}$ (manufactured by Wako) was dissolved in phosphate buffer (pH 7.4) and shaken at 37° C. for 72 hours, to obtain 1 mg/mL of a suspension (hereinafter referred to as amyloid suspension in this Example) of aggregated Aβ (hereinafter referred to as amyloid in this Example).

(2) According to the method described in a literature (Naiki, H., et al., Laboratory Investigation 74, p. 374-383 (1996)), the amyloid suspension was subjected to qualitative experiment based on fluorescence spectrophotometric method using Thioflavin T (manufactured by Fluka) to confirm that the aggregated Aβ obtained in (1) was amyloid (measurement conditions: excitation wavelength of 446 nm, and emission wavelength of 490 nm).

(3) According to the method described in a literature (Wang, Y., et al., J. Labeled Compounds Radiopharmaceut. 44, S239 (2001)), [$^{125}$I]2-(3'-iodo-4'-aminophenyl)benzothiazole (hereinafter referred to as [$^{125}$I]3'-BTA-O) was prepared from a labeling precursor 2-(4'-aminophenyl)benzothiazole, and dissolved in ethanol. As Congo Red, Thioflavin T and 6-methyl-2-[4'-(N,N-dimethylamino)phenyl]benzothiazole (hereinafter referred to as 6-Me-BTA-2), commercially available reagents were weighed and used as they were.

(4) IMPY was synthesized according to the method described in a literature (Zhuang, Z. P., et al., J. Med. Chem. 46, 237 (2003)).

(5) Each compound for evaluation or ethanol solution thereof, an ethanol solution of [$^{125}$I]3'-I-BTA-O prepared above in (3) and an amyloid suspension prepared above in (1) were dissolved in 1% bovine serum albumin-containing phosphate buffer (pH 7.4), and samples having final concentrations of each compound for evaluation, [$^{125}$I]3'-I-BTA-0 and amyloid shown in Table 2 respectively was prepared.

TABLE 2

Final concentrations of each compound in sample solutions

| Experiment | Compound for evaluation | Concentration of compound for evaluation | [$^{125}$I]3'-I-BTA-0 concentration | Amyloid |
|---|---|---|---|---|
| Comparative Example 1 | Congo Red | Each concentration of 0, 0.001, 0.01, 0.1, 1, 10, 100, 1000 nmol/L | 400 pmol/L | 1 μmol/L |
| Comparative Example 2 | Thioflavin T | | | |
| Comparative Example 3 | IMPY | | | |
| Example 7 | Compound 3 | | | |

(6) Each sample solution prepared above in (5) was filled in each well (about 0.3 mL in volume) of a 96-well microplate. The microplate filled with the sample solutions was shaken at a given rate (400 rpm) at 22° C. for 3 hours. Then, each sample solution was filtered through a glass fiber filter (trade name: Mulutiscreen™-FC, manufactured by Millipore), to separate the [$^{125}$I]3'-I-BTA-0 attached to amyloid from the free [$^{125}$I]I-BTA-0.

(7) The glass fiber filter used for the filtration of each sample solution was washed with 1% bovine serum albumin-containing phosphate buffer (pH 7.4) (0.5 mL×5), and radioactivity of the glass fiber filter was measured with an autowell gamma system (manufactured by Aloka, Type: ARC-301B) (hereinafter, A denotes the radioactivity level in a sample with zero (0) concentration of each compound for evaluation, and B denotes the radioactivity level in a sample with 0.001 nmol/L or higher concentration of each compound for evaluation).

(8) Separately, a solution containing 15 μmol/L of 6-Me-BTA-2, 400 pmol/L of [$^{125}$I]3'-I-BTA-O and 1 μmol/L of amyloid were prepared and subjected to the same procedures as described above in (7) and (8) to measure a radioactivity level. The measured radioactivity level was defined as the background radioactivity level, and used in the calculation of the inhibition ratio (hereinafter referred to as BG).

(9) Using the radioactivity levels measured above in (7) and (8), the inhibition ratio was determined by the following formula (1).

$$\frac{B - BG}{A - BG} \times 100\,(\%) \qquad (1)$$

A graph in which values converted by probit transformation from the obtained inhibition ratios were plotted relative to logarithms of concentrations of compounds for evaluation was prepared to obtain an approximate straight line by the least square method. Using the line, a 50% inhibition concentration of each compound for evaluation (hereinafter referred to as $IC_{50\%}$ value) was determined. Using the value as an indicator, affinity of each compound for evaluation with amyloid was evaluated.

$IC_{50\%}$ value of each compound for evaluation is shown in Table 3. Compounds 3 showed $IC_{50\%}$ values of less than 100 and had significantly higher affinity with amyloid than Congo Red and Thioflavin T which are generally known to have affinity with amyloid. The results show that Compounds 3 has good affinity with amyloid like IMPY.

TABLE 3

$IC_{50\%}$ values of the present compounds

| Experiment | Compound for evaluation | $IC_{50\%}$ values (nmol/L) |
|---|---|---|
| Comparative Example 1 | Congo Red | >1000 |
| Comparative Example 2 | Thioflavin T | >1000 |
| Comparative Example 3 | IMPY | 25.8 |
| Example 7 | Compound 3 | 66.9 |

Example 8 to 9, Comparative Example 4

Measurement of Partition Coefficient Based on the Octanol Extraction Method

Partition coefficients based on the octanol extraction method (hereinafter referred to as log $P_{octanol}$) were measured, which are generally known as an indicator of permeability of compounds through the blood-brain barrier (hereinafter referred to as BBB).

A diethyl ether solution of Compound 1 prepared in Example 3 (Example 8), a diethyl ether solution of Compound 2 prepared in Example 6 (Example 9), and a diethyl ether solution of [$^{123}$I]-IMPY prepared in Reference Example 1 (Comparative Example 4) were each diluted with 10 mg/mL ascorbic acid-containing physiological saline solution, and adjusted to a radioactive concentration of 20-30 MBq/mL. To 2 mL of octanol, 10 μL each of the prepared sample solutions was added, 2 mL of 10 mmol/L phosphate buffer (pH 7.4) was added, followed by stirring for 30 seconds. After the mixture was centrifuged with a low-speed centrifuge (2000 rpm×60 min.), the octanol layer and the water layer were sampled each in an amount of 1 mL, and subjected to measurement of radioactivity count with an autowell gamma system (Type: ARC-301B, manufactured by Aloka). Using the obtained radioactivity count, log $P_{octanol}$ was calculated in accordance with the equation (2).

$$\log P_{octanol} = \log_{10}\left(\frac{\text{Radioactivity count of octanol layer}}{\text{Ratioactivity count of water layer}}\right) \qquad (2)$$

The results are shown in Table 4. All the compounds showed log $P_{octanol}$ values between 1 and 3. It is known that compounds permeable to BBB show a log $P_{octanol}$ value between 1 and 3 (Douglas D. Dischino et al., J. Nucl. Med., (1983), 24, p. 1030-1038). From the above results, it is implied that both compounds have a BBB permeability like IMPY.

TABLE 4 logP$_{octanol}$ value of the present compound

| Experiment | Compound | logP$_{octanol}$ value |
|---|---|---|
| Comparative Example 4 | [$^{123}$I]-IMPY | 1.9 |
| Example 8 | Compound 1 | 1.8 |
| Example 9 | Compound 2 | 2.1 |

Example 10 to 11, Comparative Example 5

Measurement of Transferability into Brain and Clearance

Using Compound 1 (Example 10) and Compound 2 (Example 11), a time course change of radioactive accumulation in brain of male Wistar rats (7-week old) was measured.

A diethyl ether solution of Compound 1 (Example 10) prepared in Example 3, a diethyl ether solution of Compound 2 (Example 11) prepared in Example 6 and a diethyl ether solution of [$^{123}$I]-IMPY (Comparative Example 5) prepared in Reference Example 1 were each diluted with 10 mg/mL ascorbic acid-containing physiological saline solution to adjust to a radioactive concentration of 8-12 MBq/mL. 0.05 mL each of the prepared sample solutions was injected under thiopental anesthesia into the tail vein of the rats. The rats were sacrificed by bleeding from abdominal artery, and brains were removed and subjected to measurement of mass of brains and further subjected to measurement of radioactivity (hereinafter referred to as A in this Example) with a single channel analyzer (detector type: SP-20 manufactured by OHYO KOKEN KOGYO Co., Ltd.) 2, 5, 30 and 60 minutes after the injection. Further, the radioactivity level of the rest of the whole body was measured in the same manner as above (hereinafter referred to as B in this Example). Using these measurement results, radioactive distribution per unit weight of brain (% ID/g) at the respective time points were calculated in accordance with the following formula (3).

Three animals were used for the experiment at the respective time points.

$$\% \ ID/g = \frac{A}{B \times \text{brain weight}} \times 100 \quad (3)$$

The results are shown in Table 5. As shown in Table 5, Compounds 1 and 2 showed a significant radioactive accumulation like [$^{123}$I]-IMPY at the time point of two minutes after the injection, and then showed a tendency to rapidly clear away in 60 minutes. These results suggest that both Compounds 1 and 2 possess excellent transferability to brain and rapid clearance from brain like [$^{123}$I]-IMPY.

TABLE 5

Radioactive distribution in brain of the present compound after intravenous injection (rats)

| | Compound | Radioactive distribution per unit weight (% ID/g) | | | |
|---|---|---|---|---|---|
| | | After 2 min. | After 5 min. | After 30 min. | After 60 min. |
| Example 10 | Compound 1 | 0.90 | 0.52 | 0.06 | 0.01 |
| Example 11 | Compound 2 | 0.89 | 0.66 | 0.13 | 0.04 |
| Comparative Example 5 | $^{123}$I-IMPY | 1.19 | 0.97 | 0.23 | 0.09 |

Comparative Example 6

Ex Vivo Autoradiogram of $^{123}$I-IMPY Using Rats of Amyloid Injected Model (1) Aβ$_{1-40}$ (manufactured by Peptide Institute, INC.) was dissolved in phosphate buffer (pH 7.4) and shaken at 37° C. for 72 hours, to obtain a 1 mg/mL suspension of aggregated Aβ (hereinafter referred to as amyloid suspension in this Example).

(2) 2.5 μL (corresponding to 25 μg) of the amyloid suspension was injected into an amygdaloid nucleus on one side of a male Wistar rat (7-week old). As a control, 2.5 μL of a phosphate buffered physiological saline solution (pH 7.4) was injected into an amygdaloid nucleus on the other side of the rat. The rats were examined 1 day after the injection of the amyloid suspension and the phosphate buffered physiological saline solution (pH 7.4).

(3) [$^{123}$I]-IMPY was dissolved in a 10 mg/mL ascorbic acid-containing physiological saline solution to obtain a sample solution (29 MBq/mL in radioactivity concentration in the sample solution). This solution was injected under thiopental anesthesia into the rat through the tail vein (dosage: 0.5 mL, dosed radioactivity: 14.5 MBq equivalent).

(4) Brain was removed 60 minutes after the injection to prepare a brain slice of 10 μm in thickness with a microtome (type: CM3050S, manufactured by LEICA). The brain slice was exposed to an imaging plate for 20 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (manufactured by NIKON Corporation; type: TE2000-Umodel; excitation wavelength: 400-440 nm; detection wavelength: 470 nm). Thus, it was confirmed that amyloid was deposited on the slice (FIG. 5b).

FIG. 5 shows images by autoradiogram and Thioflavin T staining of the brain slice of the rat to which amyloid was injected intracerebrally. As shown in this figure, a marked accumulation of radioactivity was observed in the amygdaloid nucleus on the side to which the amyloid suspension was injected, but also non-specific accumulation was observed in white matter where amyloid was not injected.

Example 12

Confirmation of Imaging of Amyloid in Brain

The following experiment was carried out in order to examine whether amyloid in brain can be imaged by the compound of the present invention.

(1) Aβ$_{1-42}$ (manufactured by Wako) was dissolved in phosphate buffer (pH 7.4) and shaken at 37° C. for 72 hours, to obtain a 1 mg/mL suspension of aggregated Aβ (hereinafter referred to as amyloid suspension in the Examples).

(2) 2.5 μL (corresponding to 25 μg) of the amyloid suspension was injected into an amygdaloid nucleus on one side of a male Wistar rat (7-week old). As a control, 2.5 μL of a phosphate buffered physiological saline solution (pH 7.4) was injected into an amygdaloid nucleus on the other side of the rat. The rats were examined 1 day after the injection of the amyloid suspension and the phosphate buffered physiological saline solution (pH 7.4).

(3) Compound 1 was dissolved in a 10 mg/mL ascorbic acid-containing physiological saline solution to obtain a sample solution (22 MBq/mL in radioactivity concentration in the sample solution). This solution was injected under thiopental anesthesia into the rat through the tail vein (dosage: 0.5 mL, dosed radioactivity: 11-13 MBq equivalent).

(4) Brain was removed 60 minutes after the injection to prepare a brain slice of 10 μm in thickness with a microtome (type: CM3050S, manufactured by LEICA). The brain slice was exposed to an imaging plate for 20 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (manufactured by NIKON Corporation; type: TE2000-U model; excitation wavelength: 400-440 nm; detection wavelength: 470 nm). Thus, it was confirmed that amyloid was deposited on the slice (FIG. 6b).

FIG. 6 shows images by autoradiogram and Thioflavin T staining of the brain slice of the rat to which amyloid was injected intracerebrally. As shown in this figure, a marked accumulation of radioactivity was observed in the amygdaloid nucleus on the side to which the amyloid suspension was injected. On the other hand, no significant accumulation of radioactivity was observed in the amygdaloid nucleus on the side to which the physiological saline solution was injected, compared with the other sites. On the autoradiogram, little accumulation of radioactivity was observed at sites other than the sites to which amyloid was injected. From the result of Thioflavin T staining, it was confirmed that amyloid was present in the site where radioactivity is accumulated (FIG. 6b).

Thus, Compound 1 showed little radioactive accumulation at the sites other than amyloid injected sites, and showed little non-specific binding to the white matter observed in [$^{123}$I]-IMPY. These results suggest that Compound 1 possesses an excellent capability of imaging amyloid in the total autoradiogram image. These results also suggest that Compound 1 is a compound that possesses a high specificity to imaging of intracerebral amyloid.

Example 13

Confirmation of Imaging of Amyloid in Brain

The same procedures as in Example 12 were performed except using a solution of Compound 2 in a 10 mg/mL ascorbic acid as a sample solution (the radioactive concentration of the sample solution was 25 MBq/mL).

FIG. 7 shows images by autoradiogram and Thioflavin T staining of the brain slice of the rat to which amyloid was injected intracerebrally. As shown in this figure, a marked accumulation of radioactivity was observed in the amygdaloid nucleus on the side to which the amyloid suspension was injected. From the result of Thioflavin T staining in the site where radioactivity was accumulated, it was confirmed that amyloid was present in the accumulation site. On the other hand, no significant accumulation of radioactivity was observed in the amygdaloid nucleus on the side to which the physiological saline solution was injected, compared with the other sites.

Compound 2 showed some radioactive accumulation in sites other than amyloid injected sites, but the accumulation was highly suppressed as compared to $^{123}$I-IMPY. As a result, the whole image was provided with a high capability of imaging amyloid.

These results suggest that Compound 2 is a compound that possesses a high specificity to imaging of intracerebral amyloid.

Example 14

Synthesis of 2-[3'-(2"-hydroxyethoxy)phenyl]-6-iodoimidazo[1,2-a]pyridine (Non-Radioactive Iodinated Form)

50 mL of ethyl acetate was added to 8.60 g (corresponding to 46.0 mmol) of cupric bromide to obtain a suspension, to which 2.50 g (corresponding to 22.0 mmol) of 3'-hydroxyacetophenone was added. Then, the resulting mixture was heated under reflux. After 2 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: hexane/ethyl acetate=2/1) to obtain 4.42 g (corresponding to 20.6 mmol) of 2-bromo-3'-hydroxyacetophenone (FIG. 8, Step 1).

987 mg (corresponding to 4.55 mmol) of 2-bromo-3'-hydroxyacetophenone and 1.00 g (corresponding to 4.55 mmol) of 2-amino-5-iodopyridine were dissolved in 50 mL of acetonitrile. The resulting solution was heated under reflux in an oil bath at 110° C. for 2 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 1 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 927 mg (corresponding to 2.76 mmol) of 2-(3'-hydroxyphenyl)-6-iodoimidazo[1,2-a] pyridine (FIG. 8, Step 2).

Separately, 2.50 g (corresponding to 20.0 mmol) of 2-bromoethanol and 2.72 g (corresponding to 40.0 mmol) of imidazole were dissolved in 10 mL of dimethylformamide, and cooled to 0° C. Then, 5.50 g (corresponding to 20.0 mmol) of t-butyldiphenylchlorosilane was added thereto. After the reaction mixture was stirred at room temperature for 18 hours, a saturated sodium chloride aqueous solution was added, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=10/1) to obtain 7.04 g (corresponding to 19.4 mmol) of 1-bromo-2-(t-butyldiphenylsiloxy)ethane (FIG. 8, Step 3).

300 mg (corresponding to 0.893 mmol) of 2-(3'-hydroxyphenyl)-6-iodoimidazo[1,2-a]pyridine was dissolved in 5.0 mL of dimethylformamide, and 370 mg (corresponding to 2.68 mmol) of potassium carbonate was added thereto. Then, 357 mg (corresponding to 0.982 mmol) of 1-bromo-2-(t-butyldiphenylsiloxy)ethane was added thereto. After the reaction mixture was stirred at 90° C. for 2 hours, a saturated sodium chloride aqueous solution was added, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=3/1) to obtain 477 mg (corresponding to 0.771 mmol) of 2-[3'-(2"-t-butyldiphenylsiloxyethoxy)phenyl]-6-iodoimidazo[1,2-a]pyridine (FIG. 8, Step 4).

477 mg (corresponding to 0.771 mmol) of 2-[3'-(2"-t-butyldiphenylsiloxyethoxy)phenyl]-6-iodoimidazo[1,2-a]pyridine was dissolved in 0.98 mL of tetrahydrofuran, and 0.93 mL of a 1.0 mol/L tetrahydrofuran solution of tetrabutylammoniumfluoride was added thereto. After the reaction mixture was stirred at room temperature for 15 minutes, ammonium chloride aqueous solution was added followed by addition of 5.0 mL of water and 2.0 mL of acetonitrile to filter precipitates. The filtered precipitates were washed with water and acetonitrile in this order to obtain 120 mg (corresponding to 0.316 mmol) of 2-[3'-(2"-hydroxyethoxy)phenyl]-6-iodoimidazo[1,2-a]pyridine (FIG. 8, Step 5).

The NMR measurement results of the resulting 2-[3'-(2"-hydroxyethoxy)phenyl]-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: dimethylsulfoxide-d6; resonance frequency: 500 MHz): δ8.91 (s, 1H), 8.35 (s, 1H), 7.52-7.51 (m, 2H), 7.45 (s, 2H), 7.35 (t, J=8.2 Hz, 1H), 6.93-6.90 (m, 1H), 4.06 (t, J=4.6 Hz, 2H), 3.75 (t, J=4.6 Hz, 2H).

Example 15

Synthesis of 6-tributylstannyl-2-[3'-(2"-hydroxyethoxy)phenyl]-imidazo[1,2-a]pyridine 70 mg (corresponding to 0.184 mmol) of 2-[3'-(2"-hydroxyethoxy)phenyl]-6-iodoimidazo[1,2-a]pyridine obtained in Example 14 was dissolved in 4.0 mL of dioxane, and 2.0 mL of triethylamine was added thereto. Then, 0.20 mL (corresponding to 0.39 mmol) of bis(tributyltin) and 14.0 mg (a catalytic amount) of tetrakis-triphenylphosphine palladium were added thereto. After the reaction mixture was stirred at 90° C. for 20 hours, the solvent was distilled off under reduced pressure. The residue was purified by flash silica gel column chromatography (elution solvent: hexane/ethyl acetate=2/1) to obtain 73.0 mg (corresponding to 0.134 mmol) of 6-tributylstannyl-2-[3'-(2"-hydroxyethoxy)phenyl]imidazo[1,2-a]pyridine (FIG. 9, Step 1).

The NMR measurement results of the resulting 6-tributylstannyl-2-[3'-(2"-hydroxyethoxy)phenyl]imidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: chloroform-dl; resonance frequency: 500 MHz): δ 7.99 (d, J=0.9 Hz, 1H), 7.82 (s, 1H), 7.64-7.50 (m, 3H), 7.34-7.31 (m, 1H), 7.18-7.17 (m, 1H), 6.90-6.87 (m, 1H), 4.20 (t, J=4.3 Hz, 2H), 3.98 (t, J=4.3 Hz, 2H), 1.69-1.48 (m, 6H), 1.39-1.32 (m, 6H), 1.19-1.05 (m, 6H), 0.91 (t, J=7.4 Hz, 9H).

Example 16

Synthesis of 2-[3'-(2"-hydroxyethoxy)phenyl]-6-[$^{123}$I]iodoimidazo[1,2-a]pyridine To 60 µL of a solution of 6-tributylstannyl-2-[3'-(2"-hydroxyethoxy)phenyl]imidazo[1,2-a]pyridine (concentration: 1 mg/mL) in a mixed solution of methanol/dimethylsulfoxide=9/1, 150 µL of 1 mol/L hydrochloric acid, 15 µL of 1 mmol/L sodium iodide, 250 µL of [$^{123}$I]sodium iodide of 274 MBq and 15 µL of 10% (w/v) hydrogen peroxide were added. After the mixed solution was left to stand at 50° C. for 10 minutes, it was subjected to HPLC under the following conditions to obtain a fraction of 2-[3'-(2"-hydroxyethoxy)phenyl]-6-[$^{123}$I]iodoimidazo[1,2-a]pyridine.

HPLC Conditions:
Column: Phenomenex Luna C18 (trade name; manufactured by Phenomenex Co.; size: 4.6×150 mm)
Mobile phase: 0.1% trifluoroacetic acid in water/0.1% trifluoroacetic acid in acetonitrile=20/80 to 0/100 (17 minutes)
Flow rate: 1.0 mL/min.
Detector: Ultraviolet visible absorptiometer (Detection wavelength: 282 nm) and radioactivity counter (manufactured by raytest: type STEFFI)

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-[3'-(2"-hydroxyethoxy)phenyl]-6-[$^{123}$I]iodoimidazo[1,2-a]pyridine. The column was rinsed with 1 mL of water, and then 1 mL of diethyl ether was passed therethrough to elute 2-[3'-(2"-hydroxyethoxy)phenyl]-6-[$^{123}$I]iodoimidazo[1,2-a]pyridine. The amount of radioactivity of the obtained compound was 112.9 MBq at the end of synthesis. Further, the TLC analysis was conducted under the following conditions, and as a result, the radiochemical purity of the compound was 97%.

TLC Analysis Conditions:
TLC plate: Silica Gel 60 $F_{254}$ (trade name; manufactured by Merck & Co., Inc.)
Mobile phase: Chloroform/methanol/triethylamine=100/1/2
Detector: Rita Star (trade name; manufactured by raytest)

Example 17

Synthesis of 2-[4'-(3"-hydroxypropoxy)phenyl]-6-iodoimidazo[1,2-a]pyridine (Non-Radioactive Iodinated Form)

50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was heated under reflux. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 10, Step 1).

987 mg (corresponding to 4.55 mmol) of 2-bromo-4'-hydroxyacetophenone and 1.00 g (corresponding to 4.55 mmol) of 2-amino-5-iodopyridine were dissolved in 50 mL of acetonitrile. The resulting solution was heated under reflux in an oil bath at 110° C. for 2 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 10 mL of water and 1 mL of methanol. Then, about 10 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 927 mg (corresponding to 2.76 mmol) of 2-(4'-hydroxyphenyl)-6-iodoimidazo[1,2-a] pyridine (FIG. 10, Step 2).

Separately, 7.0 g (corresponding to 50.4 mmol) of 2-bromopropanol and 6.86 g (corresponding to 101 mmol) of imidazole were dissolved in 50 mL of dimethylformamide, and cooled to 0° C. Then, 7.59 g (corresponding to 50.4 mmol) of t-butyldimethylchlorosilane was added thereto. After the reaction mixture was stirred at room temperature for 24 hours, it was supplemented with a saturated sodium chloride aqueous solution, and extracted three times with diethyl ether. The combined diethyl ether layers were dried over anhydrous magnesium sulfate, and concentrated under reduced pressure. The resulting crude product was purified by vacuum distillation (100° C., 70 mmHg), to obtain 7.23 g (corresponding to 30.2 mmol) of 1-bromo-3-(t-butyldimethylsiloxy)propane (FIG. 10, Step 3).

2.00 g (corresponding to 5.95 mmol) of 2-(4'-hydroxyphenyl)-6-iodoimidazo[1,2-a]pyridine was dissolved in 30.0 mL of dimethylformamide, and 2.47 g (corresponding to 17.9 mmol) of potassium carbonate was added. Then, 1.51 g (corresponding to 5.95 mmol) of 1-bromo-3-(t-butyldimethylsiloxy)propane was added thereto. After the reaction mixture was stirred at room temperature for 8 days, it was supplemented with a saturated sodium chloride aqueous solution, and extracted three times with ethyl acetate. The combined ethyl acetate layers were dried over anhydrous sodium sulfate, and concentrated under reduced pressure. The resulting crude product was purified by silica gel column chromatography (elution solvent: hexane/ethyl acetate=1/1) to obtain 1.52 g (corresponding to 2.99 mmol) of 2-[4'-(3"-t-butyldimethylsiloxypropoxy)phenyl]-6-iodoimidazo[1,2-a]pyridine (FIG. 10, Step 4).

1.52 g (corresponding to 2.99 mmol) of 2-[4'-(3"-t-butyldimethylsiloxypropoxy)phenyl]-6-iodoimidazo[1,2-a]pyridine was dissolved in 5.0 mL of tetrahydrofuran, and 2.99 mL of a 1.0 mol/L tetrahydrofuran solution of tetrabutylammoniumfluoride was added thereto. After the reaction mixture was stirred at room temperature for 30 minutes, ammonium chloride solution was added followed by the addition of 10 mL of water and 5.0 mL of acetonitrile to filter precipitates. The filtered precipitates were washed with water and acetonitrile in this order, to obtain 1.03 g (corresponding to 2.61 mmol) of 2-[4'-(3"-hydroxypropoxy)phenyl]-6-iodoimidazo[1,2-a]pyridine (FIG. 10, Step 5).

The NMR measurement results of the resulting 2-[4'-(3"-hydroxypropoxy)phenyl]-6-iodoimidazo[1,2-a]pyridine (internal standard: tetramethylsilane) are shown below.

NMR apparatus employed: JNM-ECP-500 (manufactured by Japan Electron Optics Laboratory Co., Ltd. (JEOL))

$^1$H-NMR (solvent: dimethylformamide-d6; resonance frequency: 500 MHz): δ 8.96 (s, 1H), 8.33 (s, 1H), 7.98 (d, J=8.7 Hz, 2H), 7.46 (s, 2H), 7.06 (d, J=8.7 Hz, 2H), 4.63 (t, J=5.0 Hz, 1H), 4.17 (t, J=6.0 Hz, 2H), 3.72 (dt, J=5.0, 6.0 Hz, 2H), 1.98 (tt, J=6.0, 6.0 Hz, 2H).

Example 18

Synthesis of 6-tributylstannyl-2-[4'-(3"-hydroxypropoxy)phenyl]-imidazo[1,2-a]pyridine 50 mL of ethyl acetate was added to 28.17 g (corresponding to 126 mmol) of cupric bromide to obtain a suspension, to which a solution of 8.18 g (corresponding to 60.0 mmol) of 4'-hydroxyacetophenone in a mixed solution of 50 mL of ethyl acetate and 50 mL of chloroform was added. Then, the resulting mixture was heated under reflux. After 5 hours, the reaction mixture was cooled down to room temperature and filtered. The resulting filtrate was concentrated under reduced pressure. The residue was dissolved in ethyl acetate and subjected to decoloring operation with addition of active charcoal. Then, the resulting solution was filtered and concentrated. The resulting crude product was purified by flash silica gel column chromatography (elution solvent: chloroform/methanol=20/1), and recrystallized from ethyl acetate/petroleum ether, to obtain 7.25 g (corresponding to 33.7 mmol) of 2-bromo-4'-hydroxyacetophenone (FIG. 11, Step 1).

2.15 g (corresponding to 10.0 mmol) of 2-bromo-4'-hydroxyacetophenone and 1.74 g (corresponding to 10.0 mmol) of 2-amino-5-bromopyridine were dissolved in 50 mL of acetonitrile. The resulting solution was heated under reflux in an oil bath at 105° C. for 6 hours. After the completion of the reaction, the reaction solution was cooled down to room temperature, and precipitates were filtered and recovered. The precipitates were washed with acetonitrile and dried under reduced pressure. The resulting crude crystals were suspended in a mixed solution of 20 mL of water and 20 mL of methanol. Then, about 25 mL of a saturated sodium hydrogencarbonate solution was added thereto, and the mixture was sonicated for 5 minutes using an ultrasonic washing machine. Precipitates were filtered and recovered from the resulting mixture, sufficiently washed with water, and dried under reduced pressure, to obtain 2.41 g (corresponding to 8.32 mmol) of 6-bromo-2-(4'-hydroxyphenyl)imidazo[1,2-a] pyridine (FIG. 11, Step 2).

1.45 g (corresponding to 5.0 mmol) of 6-bromo-2-(4'-hydroxyphenyl)imidazo[1,2-a]pyridine that was sufficiently dried to remove moisture was dissolved in 50 mL of N,N-dimethylformamide, and 2.07 g (corresponding to 15.0 mmol) of potassium carbonate was added thereto. The mixture was supplemented with 680 µL (corresponding to 7.5 mmol) of 3-bromo-1-propanol, and then the solution was stirred at room temperature for 17 hours. After the completion of the reaction, the reaction solution was poured into water and extracted three times with chloroform. The combined chloroform layer was washed with a saturated sodium chloride solution, dried over anhydrous sodium sulfate, filtered and concentrated. The resulting crude product was recrystallized from methanol to obtain 1.28 g (corresponding to 3.67 mmol) of 6-bromo-2-[4'-(3"-hydroxypropoxy)phenyl]imidazo[1,2-a]pyridine (FIG. 11, Step 3).

100 mg (corresponding to 0.288 mmol) of 6-bromo-2-[4'-(3"-hydroxypropoxy)phenyl]imidazo[1,2-a]pyridine was dissolved in 4.0 mL of dioxane, and 2.0 mL of triethylamine was added thereto. Then, 0.22 mL (corresponding to 0.43 mmol) of bis(tributyltin) and 22.0 mg (a catalytic amount) of tetrakis-triphenylphosphine palladium were added thereto. After the reaction mixture was stirred at 90° C. for 24 hours, the solvent was distilled off under reduced pressure, and the residue was purified by flash silica gel column chromatography (elution solvent: hexane/ethyl acetate=3/1) to obtain 68.0 mg (corresponding to 0.122 mmol) of 6-tributylstannyl-2-[4'-(3"-hydroxypropoxy)phenyl]imidazo[1,2-a]pyridine (FIG. 11, Step 4).

The NMR measurement results of the resulting 6-tributylstannyl-2-[4'-(3"-hydroxypropoxy)phenyl]imidazo[1,2-a] pyridine (internal standard: tetramethylsilane) are shown below.

NMR apparatus employed: JNM-ECP-500 (manufactured by Japan Electron Optics Laboratory Co., Ltd. (JEOL))

¹H-NMR (solvent: chloroform-dl; resonance frequency: 500 MHz): δ 7.97 (s, 1H), 7.88 (d, J=8.3 Hz, 2H), 7.74 (s, 1H), 7.58 (d, J=8.3 Hz, 1H), 7.14 (d, J=8.7 Hz, 1H), 6.98 (d, J=8.7 Hz, 2H), 4.18 (t, J=6.0 Hz, 2H), 3.89 (t, J=6.0 Hz, 2H), 2.08 (tt, J=6.0, 6.0 Hz, 2H), 1.59-1.49 (m, 6H), 1.39-1.31 (m, 6H), 1.18-1.05 (m, 6H), 0.90 (t, J=7.3 Hz, 9H).

Example 19

Synthesis of 2-[4'-(3"-hydroxypropoxy)phenyl]-6-[$^{123}$I]iodoimidazo[1,2-a]pyridine To 100 μL of a solution of 6-tributylstannyl-2-[4'-(3"-hydroxypropoxy)phenyl]imidazo[1,2-a]pyridine (concentration: 1 mg/mL) in a mixed solution of methanol/dimethylsulfoxide (in a ratio of 9/1), 80 μL of 2 mol/L hydrochloric acid, 15 μL of 1 mmol/L sodium iodide, 120 μL of [$^{123}$I]sodium iodide of 414 MBq and 20 μL of 10% (w/v) hydrogen peroxide were added. After the mixed solution was left to stand at 50° C. for 10 minutes, the solution was subjected to HPLC under the following conditions, to obtain a fraction of 2-[4'-(3"-hydroxypropoxy)phenyl]-6-[$^{123}$I]iodoimidazo[1,2-a]pyridine.

HPLC Conditions:
Column: Phenomenex Luna C18 (trade name; manufactured by Phenomenex Co.; size: 4.6×150 mm)
Mobile phase: 0.1% trifluoroacetic acid in water/0.1% trifluoroacetic acid in acetonitrile=80/20 to 0/100 (17 minutes)
Flow rate: 1.0 mL/min.
Detector: Ultraviolet visible absorptiometer (Detection wavelength: 282 nm) and radioactivity counter (manufactured by raytest: type STEFFI)

10 ml of water was added to the fraction. The resulting solution was passed through a reversed phase column (trade name: Sep-Pak (registered trademark) Light C8 Cartridges manufactured by Waters: the packed amount of the packing agent: 145 mg) so that the column adsorbs and collects 2-[4'-(3"-hydroxypropoxy)phenyl]-6-[$^{123}$I]iodoimidazo[1,2-a]pyridine. The column was rinsed with 1 mL of water, and then 1 mL of diethyl ether was passed therethrough to elute 2-[4'-(3"-hydroxypropoxy)phenyl]-6-[$^{123}$I]iodoimidazo[1,2-a]pyridine. The amount of radioactivity of the obtained compound was 219 MBq at the end of synthesis. Further, the TLC analysis was conducted under the following conditions, and as a result, the radiochemical purity of the compound was 97%.

TLC Analysis Conditions:
TLC plate: Silica Gel 60 F$_{254}$ (trade name; manufactured by Merck & Co., Inc.)
Mobile phase: Chloroform/methanol/triethylamine=100/1/2
Detector: Rita Star (trade name; manufactured by raytest)

Example 20 to 21, Comparative Example 7

Measurement of Partition Coefficient Based on the Octanol Extraction Method

A diethyl ether solution (Example 20) of Compound 4 prepared in Example 16, a diethyl ether solution (Example 21) of Compound 6 prepared in Example 19, and a diethyl ether solution (Comparative Example 7) of [$^{123}$I]-IMPY were each diluted with a 10 mg/mL ascorbic acid-containing physiological saline solution to adjust to a radioactive concentration of 20-30 MBq/mL. To 2 mL of octanol, 10 μL each of the prepared sample solution was added, and 2 mL of 10 mmol/L phosphate buffer (pH 7.4) was further added, followed by stirring for 30 seconds. After the mixture was centrifuged with a low-speed centrifuge (2000 rpm×60 min.), the octanol layer and the water layer were sampled each in an amount of 1 mL, and subjected to measurement of radioactivity count with an autowell gamma system (Type: ARC-301B, manufactured by Aloka). Using the obtained radioactivity count, log P$_{octanol}$ was calculated in accordance with the equation (4).

$$\log P_{octanol} = \log_{10}\left(\frac{\text{Radioactivity count of octanol layer}}{\text{Ratioactivity count of water layer}}\right) \quad (4)$$

The results are shown in Table 6. All the compounds showed log P$_{octanol}$ values between 1 and 3. It is known that compounds permeable to BBB show a log P$_{octanol}$ value between 1 and 3 (Douglas D. Dischino et al., J. Nucl. Med., (1983), 24, p. 1030-1038). From the above results, it is implied that both compounds have a BBB permeability comparable to IMPY.

TABLE 6

| logP$_{octanol}$ value of the present compound | | |
|---|---|---|
| Experiment | Compound | logP$_{octanol}$ value |
| Comparative Example 7 | [$^{123}$I]-IMPY | 2.1 |
| Example 20 | Compound 4 | 2.5 |
| Example 21 | Compound 6 | 2.1 |

Example 22 to 23, Comparative Example 8

Measurement of Transferability into Brain and Clearance

Using Compound 4 and Compound 6, a time course change of radioactive accumulation in brain of male Wistar rats (7-week old) was measured.

Compound 4 (Example 22), Compound 6 (Example 23) and a solution of [$^{123}$I]-IMPY (Comparative Example 8) prepared above in Reference Example 1 were each diluted with a 10 mg/mL ascorbic acid-containing physiological saline solution to prepare solutions (20-31 MBq/mL in radioactive concentration). 0.05 mL each of the prepared sample solutions was injected under thiopental anesthesia into the tail vein of the respective Wistar rat (7-week old). The rats were sacrificed by bleeding from abdominal artery, and brains were removed and subjected to measurement of mass of brains and further subjected to measurement of radioactivity (hereinafter referred to as A in this Example) with a single channel analyzer (detector type: SP-20 manufactured by OHYO KOKEN KOGYO Co., Ltd.) 2, 5, 30 and 60 minutes after the injection. Further, the radioactivity level of the rest of the whole body was measured in the same manner as above (hereinafter referred to as B in this Example). Using these measurement results, radioactive distribution per unit weight of brain (% ID/g) at the respective time points were calculated in accordance with the following formula (5).

Three animals were used for the experiment at the respective time points.

$$\% \ ID/g = \frac{A}{B \times \text{brain weight}} \times 100 \quad (5)$$

The results are shown in Table 7. As shown in Table 7, Compounds 4 and 6 showed a significant accumulation like [$^{123}$I]-IMPY at the time point of two minutes after the injection, and then showed a tendency to rapidly clear away in 60 minutes. These results suggest that Compounds 4 and 6 possess high transferability to brain and rapid clearance from brain like [$^{123}$I]-IMPY.

TABLE 7

Radioactive distribution in brain of the present compound after intravenous injection (rats)

| | | Radioactive distribution per unit weight (% ID/g) | | | |
|---|---|---|---|---|---|
| | Compound | After 2 min. | After 5 min. | After 30 min. | After 60 min. |
| Example 22 | Compound 4 | 0.56 | 0.28 | 0.04 | 0.01 |
| Example 23 | Compound 6 | 0.81 | 0.56 | 0.07 | 0.02 |
| Comparative Example 8 | $^{123}$I-IMPY | 1.19 | 0.97 | 0.23 | 0.09 |

Example 24 to 25

Confirmation of Imaging of Amyloid in Brain (1) Aβ$_{1-42}$ (manufactured by Wako) was dissolved in phosphate buffer (pH 7.4) and shaken at 37° C. for 72 hours, to obtain 1 mg/mL of a suspension of aggregated Aβ (hereinafter referred to as amyloid suspension in the Examples).

(2) 2.5 μL (corresponding to 25 μg) of the amyloid suspension was injected into an amygdaloid nucleus on one side of a male Wistar rat (7-week old). As a control, 2.5 μL of a phosphate buffered physiological saline solution (pH 7.4) was injected into an amygdaloid nucleus on the other side of the rat. The rats were examined 1 day after the injection of the amyloid suspension and the phosphate buffered physiological saline solution (pH 7.4).

(3) A sample solution (30 MBq/mL in radioactivity concentration, Example 24) in which Compound 4 was dissolved in a 10 mg/mL ascorbic acid-containing physiological saline solution and a sample solution (30 MBq/mL in radioactivity concentration, Example 25) in which Compound 6 was dissolved in a 10 mg/mL ascorbic acid-containing physiological saline solution were prepared. This solution was injected under thiopental anesthesia into the rat through the tail vein (dosage: 0.5 mL, dosed radioactivity: 11-15 MBq equivalent).

(4) Brain was removed 60 minutes after the injection to prepare a brain slice of 10 μm in thickness with a microtome (type: CM3050S, manufactured by LEICA). The brain slice was exposed to an imaging plate for 20 hours, and then image analysis was carried out by use of a Bio-imaging Analyzer (type: BAS-2500; manufactured by FUJIFILM Corporation).

(5) After the completion of the image analysis using the Bio-imaging Analyzer, pathological staining with Thioflavin T was carried out to perform imaging by use of a fluorescence microscope (manufactured by NIKON Corporation; type: TE2000-Umodel; excitation wavelength: 400-440 nm; detection wavelength: 470 nm). Thus, it was confirmed that amyloid was deposited on the slice (FIG. 12 and FIG. 13).

FIG. 12 and FIG. 13 show images by autoradiogram and Thioflavin T staining of the brain slice of the rat to which amyloid was injected intracerebrally. As shown in these figures, a marked accumulation of radioactivity was observed in the amygdaloid nucleus on the side to which the amyloid suspension was injected, in both cases where Compounds 4 and 6 were administered. On the other hand, no significant accumulation of radioactivity was observed in the amygdaloid nucleus on the side to which the physiological saline solution was injected, compared with the other sites. On the autoradiogram, little accumulation of radioactivity was observed at sites other than the site to which amyloid was injected. From the result of Thioflavin T staining, it was confirmed that amyloid was present in the site where radioactivity was accumulated (FIG. 12 and FIG. 13). These results suggest that Compounds 4 and 6 possess a property of accumulating on intracerebral amyloid and a capability of imaging intracerebral amyloid.

Example 26 to 28

Reverse Mutation Test

In order to examine gene mutagenicity of Compound 3, 5 and 8, reverse mutation test using *Salmonella typhimurium* TA98 and TA100 (hereinafter referred to as Ames test) was conducted.

The test was conducted without addition of S9mix and with addition of S9mix. Dimethylsulfoxide (DMSO) was used as a negative control. A positive control was 2-(2-furyl)-3-(5-nitro-2-furyl)acrylamide (hereinafter referred to as AF-2) in case S9mix was not added, and 2-aminoanthracene (hereinafter referred to as 2-AA) in case S9mix was added.

As a sample solution to be added to a test plate, each compound was dissolved in DMSO to prepare a solution at a concentration of 50 mg/mL, and further, each solution was diluted with DMSO to prepare a solution with 7 dosage (geometric ratio 3). As a sample solution for preparing a sample of positive control, when TA98 was used as a test strain without addition of S9mix, a solution of AF-2 (compound concentration: 1 μg/mL) in DMSO was prepared; when TA100 was used as a test strain without addition of S9mix, a solution of AF-2 (compound concentration: 0.1 μg/mL) in DMSO was prepared; when TA98 was used as a test strain with addition of S9mix, a solution of 2-AA (compound concentration: 5 μg/mL) in DMSO was prepared; and when TA100 was used as a test strain with addition of S9mix, a solution of 2-AA (compound concentration: 10 μg/mL) in DMSO was prepared.

After each sample solution to be examined and a test strain (TA98 or TA100) were mixed together so as to make the addition amount of each sample to be 0.1 mL/plate, the mixture was multilayered using soft agar on a medium of a test plate, and then incubated at 37° C. for 48 hours. Separately, after each sample solution to be examined, S9mix and a test strain were mixed together so as to make the addition amount of each sample to be 0.1 mL/plate, the mixture was multilayered using soft agar on a medium of a test plate, and then incubated at 37° C. for 48 hours. On the other hand, only DMSO was used as a sample solution to perform the same procedure as above for the negative control. Judgment was made by counting the number of reverse mutation colonies on the plate after the incubation, and when the number of reverse mutation colonies was not less than two times the number in negative control and showed concentration-dependent increase, mutagenicity was determined to be positive.

TABLE 8

Results of Ames test

| | | Mutagenicity | | | |
|---|---|---|---|---|---|
| | | Without addition of S9mix | | With addition of S9mix | |
| | Compound | TA98 | TA100 | TA98 | TA100 |
| Example 26 | Compound 3 | Negative | Negative | Negative | Negative |
| Example 27 | Compound 5 | Negative | Negative | Negative | Negative |
| Example 28 | Compound 8 | Negative | Negative | Negative | Negative |

INDUSTRIAL APPLICABILITY

The compounds of the present invention can be utilized in the field of diagnostic agents.

Figure 1:
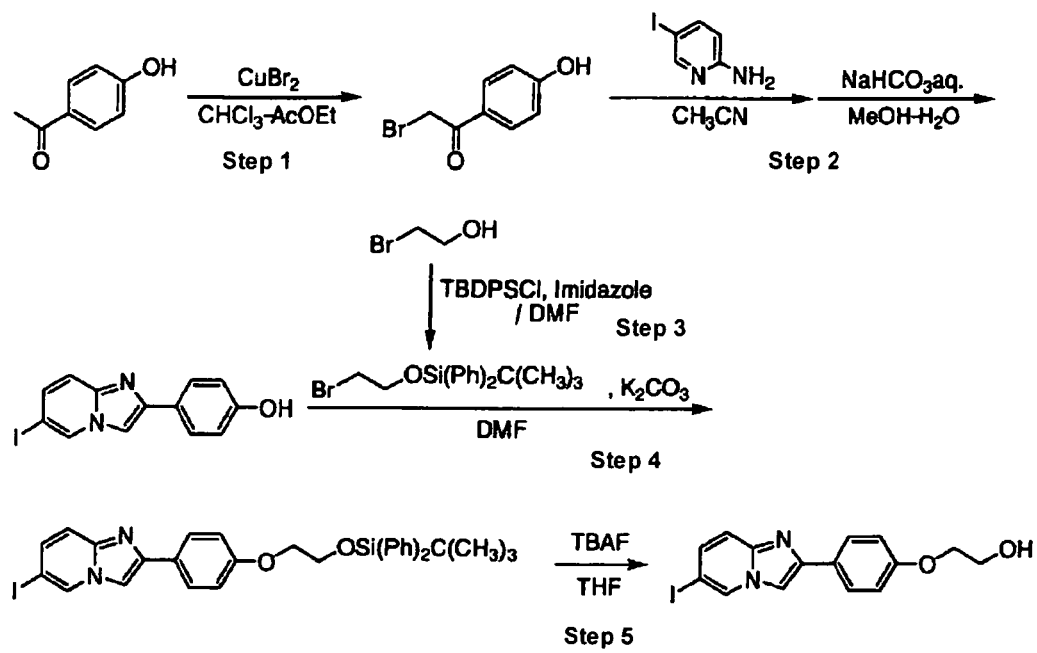
FIG. 1 is a scheme of synthesis of 2-[4'-(2-hydroxyethoxy)phenyl]-6-iodoimidazo[1,2-a]pyridine (non-radioactive iodinated form).
Figure 2:
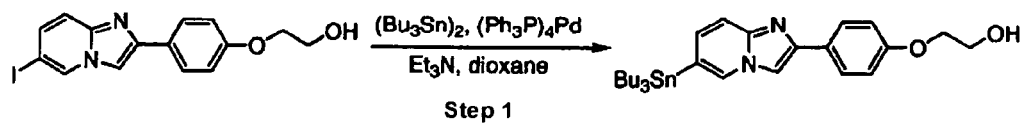
FIG. 2 is a scheme of synthesis of 6-tributylstannyl-2-[4'-(2"-hydroxyethoxy)phenyl]-imidazo[1,2-a]pyridine.
Figure 3:
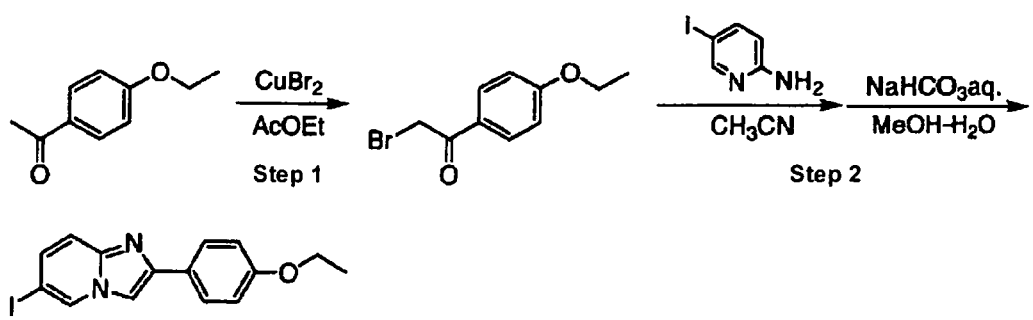
FIG. 3 is a scheme of synthesis of 2-(4'-ethoxyphenyl)-6-iodoimidazo[1,2-a]pyridine (non-radioactive iodinated form).
Figure 4:
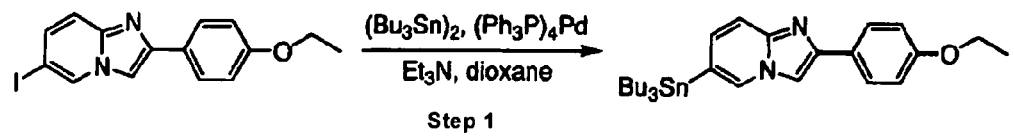
FIG. 4 is a scheme of synthesis of 6-tributylstannyl-2-(4'-ethoxyphenyl)imidazo[1,2-a]pyridine.
Figure 5:
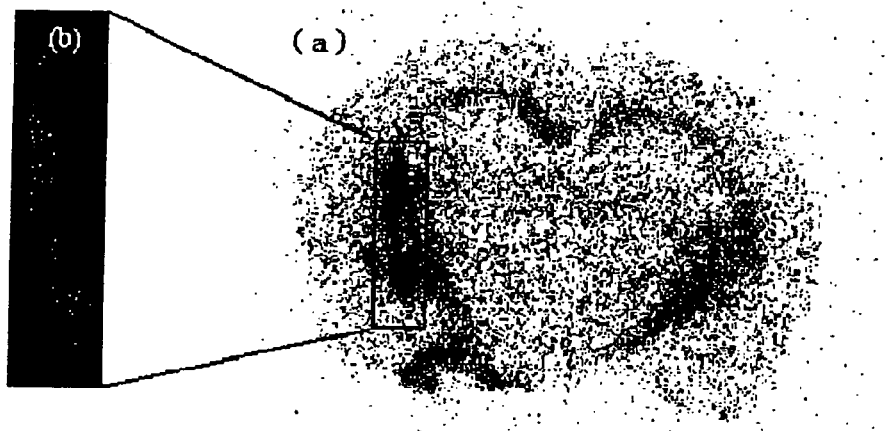
FIG. 5(a) is an autoradiogram of the brain slice after the injection of $^{123}$I-IMPY.
FIG. 5(b) is a fluorescent microscopic image of the Thioflavin T stained sample (a magnification of the site to which the amyloid suspension was injected).
Figure 6:
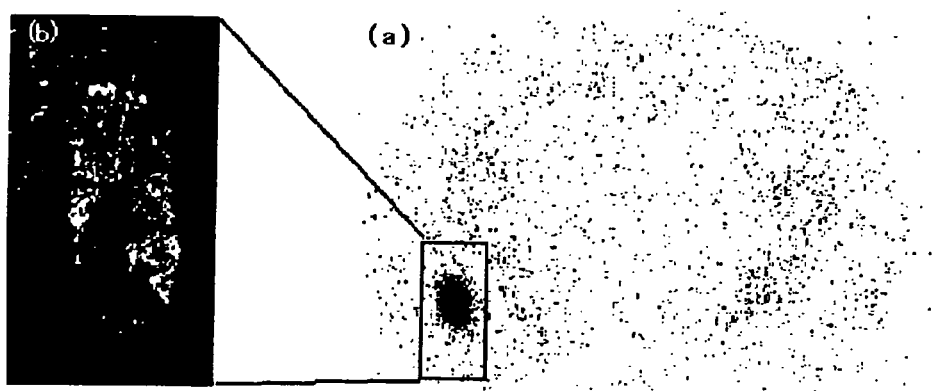
FIG. 6(a) is an autoradiogram of the brain slice after the injection of 2-[4'-(2"-hydroxyethoxy)phenyl]-6-[$^{123}$I]iodoimidazo[1,2-a]pyridine.
FIG. 6(b) is a fluorescent microscopic image of the Thioflavin T stained sample (a magnification of the site to which the amyloid suspension was injected).
Figure 7:
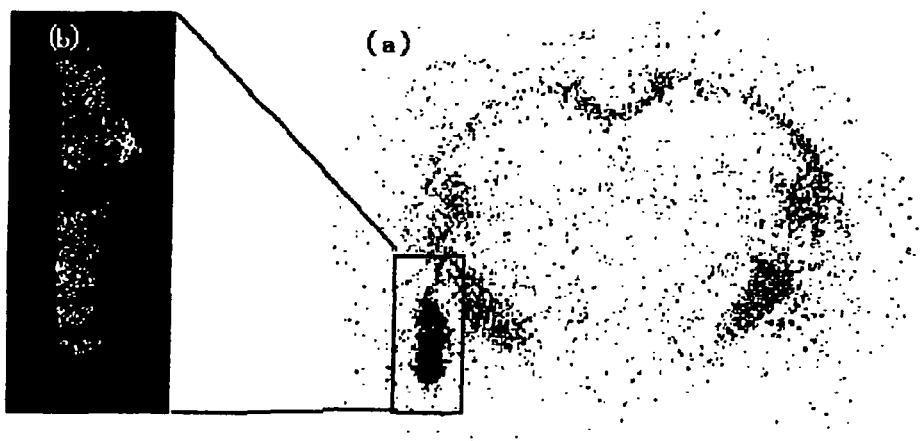
FIG. 7(a) is an autoradiogram of the brain slice after the injection of 2-(4'-ethoxyphenyl)-6-[$^{123}$I]iodoimidazo[1,2-a]pyridine.
FIG. 7(b) is a fluorescent microscopic image of the Thioflavin T stained sample (a magnification of the site to which the amyloid suspension was injected).
Figure 8:
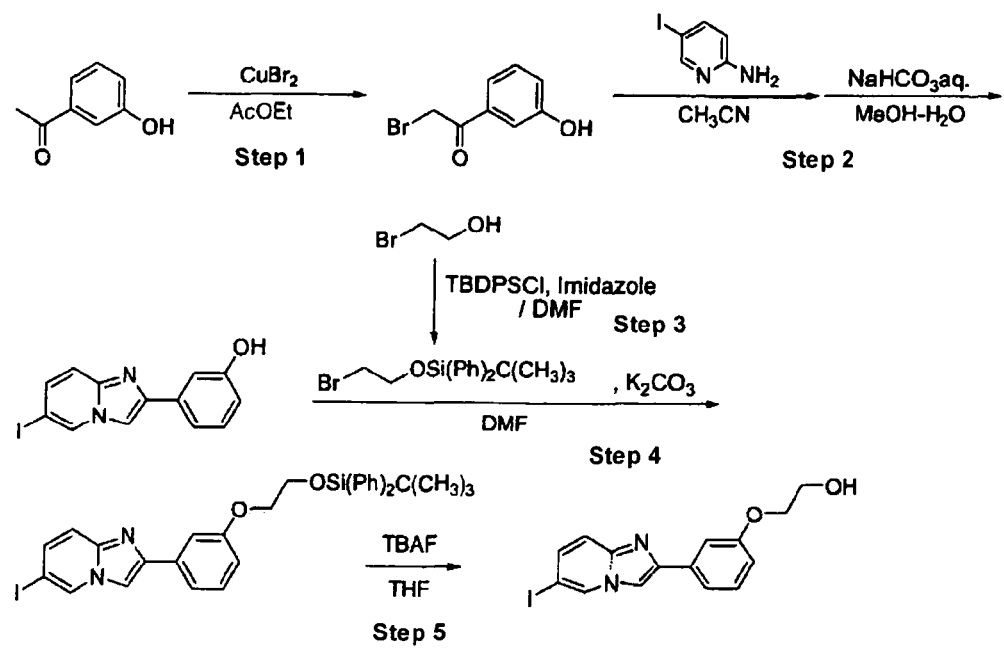
FIG. 8 is a scheme of synthesis of 2-[3'-(2"-hydroxyethoxy)phenyl]-6-iodoimidazo[1,2-a]pyridine (non-radioactive iodinated form).
Figure 9:
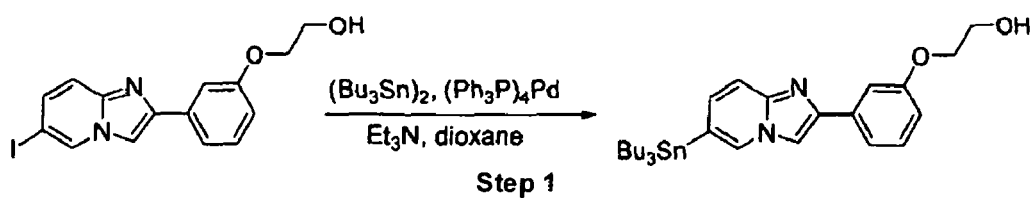
FIG. 9 is a scheme of synthesis of 6-tributylstannyl-2-[3'-(2"-hydroxyethoxy)phenyl]-imidazo[1,2-a]pyridine.
Figure 10:
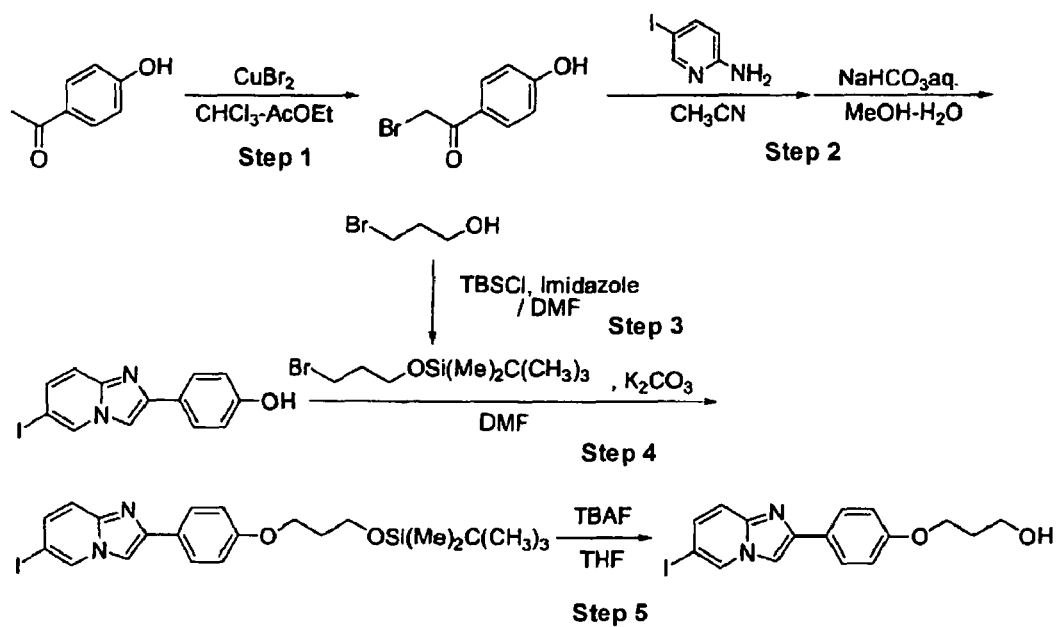
FIG. 10 is a scheme of synthesis of 2-[4'-(3"-hydroxypropoxy)phenyl]-6-iodoimidazo[1,2-a]pyridine (non-radioactive iodinated form).
Figure 11:
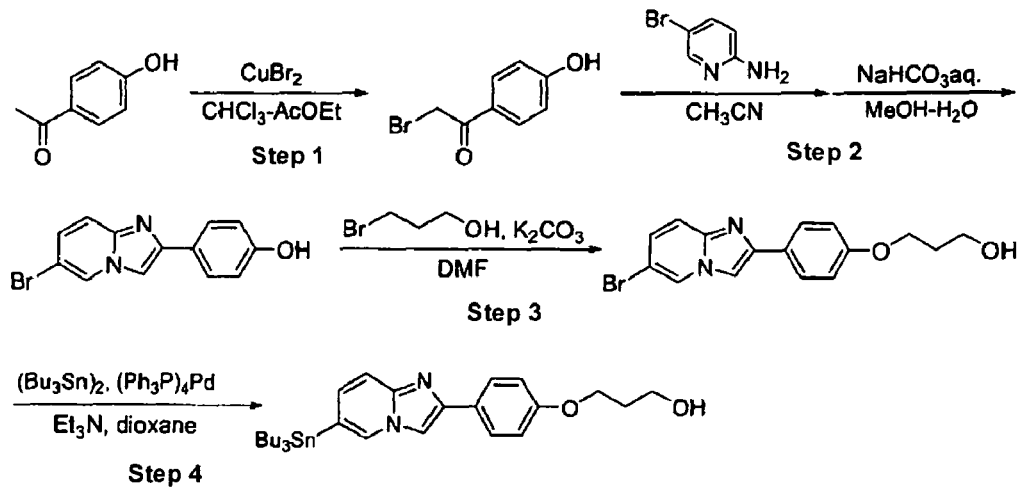
FIG. 11 is a scheme of synthesis of 6-tributylstannyl-2-[4'-(3"-hydroxypropoxy)phenyl]-imidazo[1,2-a]pyridine.
Figure 12:
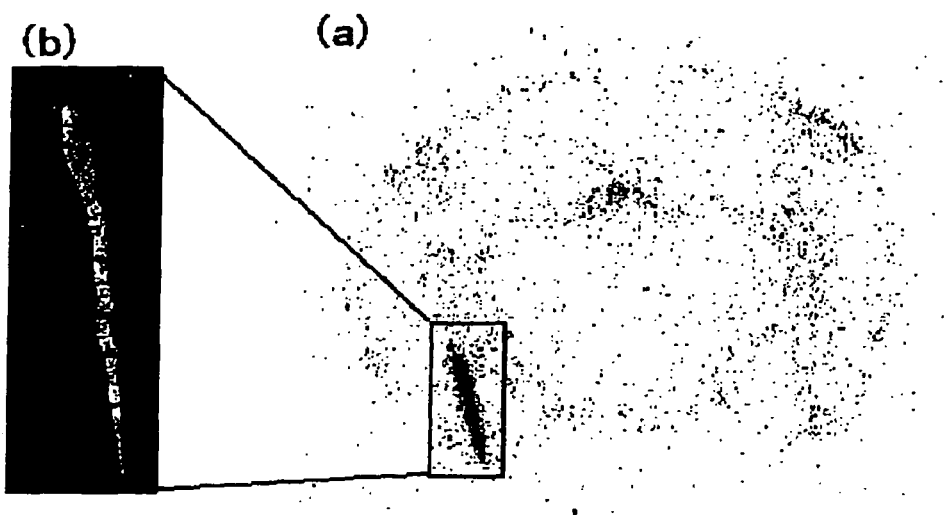
FIG. 12(a) is an autoradiogram of the brain slice after the injection of Compound 4.
FIG. 12(b) is a fluorescent microscopic image of the Thioflavin T stained sample (a magnification of the site to which the amyloid suspension was injected).
Figure 13:
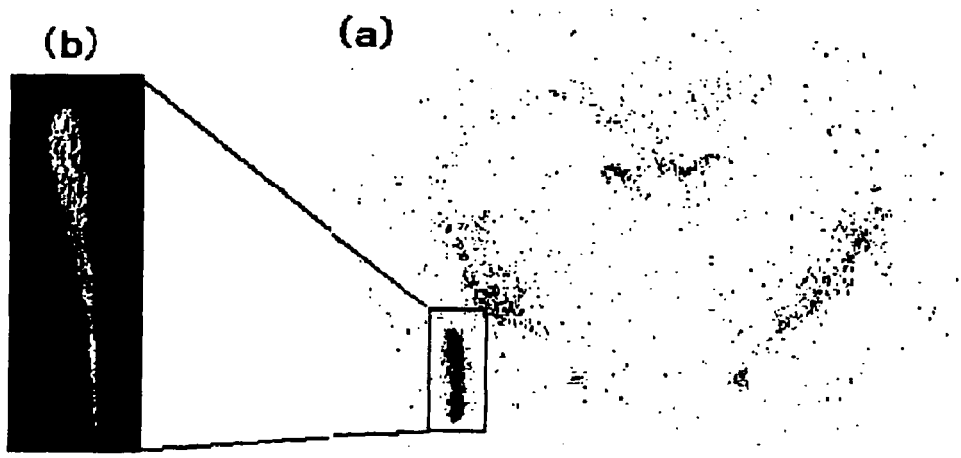
FIG. 13(a) is an autoradiogram of the brain slice after the injection of Compound 6.
FIG. 13(b) is a fluorescent microscopic image of the Thioflavin T stained sample (a magnification of the site to which the amyloid suspension was injected).

The invention claimed is:

1. A compound represented by the following formula (1), or a salt thereof:

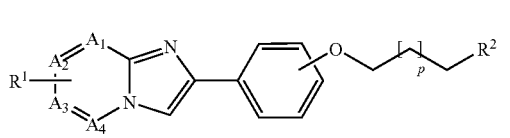

wherein each of $A_1$, $A_2$, $A_3$ and $A_4$ independently represents a carbon, $R^1$ is a radioactive halogen substituent, $R^2$ is a group selected from the group consisting of hydrogen, a hydroxyl group, a methoxy group, a carboxyl group, an amino group, an N-methylamino group, an N,N-dimethylamino group and a cyano group, and p is an integer of 0 to 2.

2. A compound represented by the following formula (2), or a salt thereof:

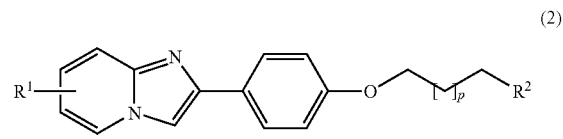

wherein $R^1$ is a radioactive halogen substituent, $R^2$ is a group selected from the group consisting of hydrogen, a hydroxyl group, a methoxy group, a carboxyl group, an amino group, an N-methylamino group, an N,N-dimethylamino group and a cyano group, and p is an integer of 0 to 2.

3. A compound or a salt thereof according to claim 1, wherein $R^2$ is a hydroxyl group.

4. A compound or a salt thereof according to claim 1, wherein $R^1$ is selected from the group consisting of $^{18}$F, $^{76}$Br, $^{123}$I, $^{124}$I, $^{125}$I and $^{131}$I.

5. A compound is selected from the group consisting of:

2-(4'-ethoxyphenyl)-6-[$^{123}$I]iodoimidazo[1,2-a]pyridine, 2-(4'-ethoxyphenyl)-6-[$^{123}$I]iodoimidazo[1,2-a]pyridine, 2-(4'-ethoxyphenyl)-6-[$^{131}$I]iodoimidazo[1,2-a]pyridine, 2-[4'-(2"-hydroxyethoxy)phenyl]-6-[$^{123}$I]iodoimidazo[1,2-a]pyridine, 2-[4'-(2"-hydroxyethoxy)phenyl]-6-[$^{125}$I]iodoimidazo[1,2-a]pyridine, 2-[4'-(2"-hydroxyethoxy)phenyl]-6-[$^{131}$I]iodoimidazo[1,2-a]pyridine, 2-[4'-(3"-hydroxypropoxy)phenyl]-6-[$^{123}$I]iodoimidazo[1,2-a]pyridine, 2-[4'-(3"-hydroxypropoxy)phenyl]-6-[$^{125}$I]iodoimidazo[1,2-a]pyridine, 2-[4'-(3"-hydroxypropoxy)phenyl]-6-[$^{131}$I]iodoimidazo[1,2-a]pyridine, 2-(4'-ethoxyphenyl)-6-[$^{123}$I]iodoimidazo[1,2-a]pyridine, 2-(4'-ethoxyphenyl)-6-[$^{125}$I]iodoimidazo[1,2-a]pyridine, 2-(4'-ethoxyphenyl)-6-[$^{131}$I]iodoimidazo[1,2-a]pyridine, 2-[3'-(2"-hydroxyethoxy)phenyl]-6-[$^{123}$I]iodoimidazo[1,2-a]pyridine, 2-[3'-(2"-hydroxyethoxy)phenyl]-6-[$^{125}$I]iodoimidazo[1,2-a]pyridine, 2-[3'-(2"-hydroxyethoxy)phenyl]-6-[$^{131}$I]iodoimidazo[1,2-a]pyridine, 2-[3'-(3"-hydroxypropoxy)phenyl]-6-[$^{123}$I]pyridine, 2-[3'-(3"-hydroxypropoxy)phenyl]-6-[$^{125}$I]iodoimidazo[1,2-a]pyridine, 2-[3'-(3"-hydroxypropoxy)phenyl]-6-[$^{131}$I]iodoimidazo[1,2-a]pyridine, or a salt thereof.

6. A compound represented by the following formula (3), or a salt thereof:

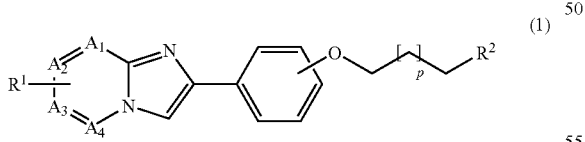
(3)

wherein each of $A_5$, $A_6$, $A_7$ and $A_8$ independently represents a carbon, $R^3$ is a group selected from the group consisting of a non-radioactive halogen substituent, a nitro group, a trialkylammonium group having alkyl chains with 1 to 4 carbon atoms, a trialkylstannyl substituent having alkyl chains with 1 to 4 carbon atoms and a triphenylstannyl group, $R^4$ is a group selected from the group consisting of hydrogen, a hydroxyl group, a methoxy group, a carboxyl group, an amino group, an N-methylamino group, an N,N-dimethylamino group and a cyano group, and q is an integer of 0 to 2.

7. A compound represented by the following formula (4), or a salt thereof:

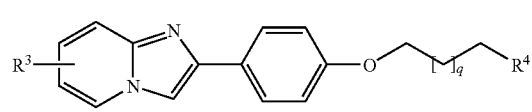
(4)

wherein $R^3$ is a group selected from the group consisting of a non-radioactive halogen substituent, a nitro group, a trialkylammonium group having alkyl chains with 1 to 4 carbon atoms, a trialkylstannyl substituent having alkyl chains with 1 to 4 carbon atoms and a triphenylstannyl group, $R^4$ is a group selected from the group consisting of hydrogen, a hydroxyl group, a methoxy group, a carboxyl group, an amino group, an N-methylamino group, an N,N-dimethylamino group and a cyano group, and q is an integer of 0 to 2.

8. A compound or a salt thereof according to claim 6, wherein $R^4$ is a hydroxyl group.

9. A diagnostic agent for Alzheimer's disease, which comprises a compound represented by the following formula (1), or a salt thereof:

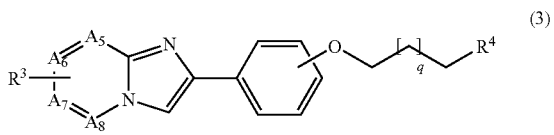
(1)

wherein each of $A_1$, $A_2$, $A_3$ and $A_4$ independently represents a carbon, $R^1$ is a radioactive halogen substituent, $R^2$ is a group selected from the group consisting of hydrogen, a hydroxyl group, a methoxy group, a carboxyl group, an amino group, an N-methylamino group, an N,N-dimethylamino group and a cyano group, and p is an integer of 0 to 2.

10. A diagnostic agent for Alzheimer's disease, which comprises a compound represented by the following formula (2), or a salt thereof:

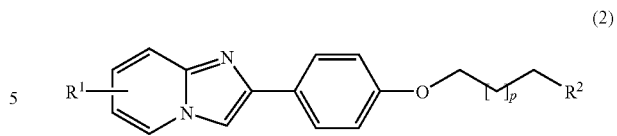
(2)

wherein $R^1$ is a radioactive halogen substituent, $R^2$ is a group selected from the group consisting of hydrogen, a hydroxyl group, a methoxy group, a carboxyl group, an amino group, an N-methylamino group, an N,N-dimethylamino group and a cyano group, and p is an integer of 0 to 2.

11. The diagnostic agent for Alzheimer's disease according to claim 9, wherein $R^4$ is a hydroxyl group.

12. The diagnostic agent for Alzheimer's disease according to claim 9, wherein $R^1$ is a radioactive halogen substituent selected from the group consisting of $^{18}F$, $^{76}Br$, $^{123}I$, $^{124}I$, $^{125}I$ and $^{131}I$.

13. The diagnostic agent for Alzheimer's disease, which comprises a compound selected from the group consisting of:
2-(4'-ethoxyphenyl)-6-[$^{123}$I]iodoimidazo[1,2-a]pyridine,
2-(4'-ethoxyphenyl)-6-[$^{123}$I]iodoimidazo[1,2-a]pyridine,
2-(4'-ethoxyphenyl)-6-[$^{131}$I]iodoimidazo[1,2-a]pyridine,
2-[4'-(2"-hydroxyethoxy)phenyl]-6-[$^{123}$I]iodoimidazo[1,2-a]pyridine,
2-[4'-(2"-hydroxyethoxy)phenyl]-6-[$^{125}$I]iodoimidazo[1,2-a]pyridine,
2-[4'-(2"-hydroxyethoxy)phenyl]-6-[$^{131}$I]iodoimidazo[1,2-a]pyridine,
2-[4'-(3"-hydroxypropoxy)phenyl]-6-[$^{123}$I]iodoimidazo[1,2-a]pyridine,
2-[4'-(3"-hydroxypropoxy)phenyl]-6-[$^{125}$I]iodoimidazo[1,2-a]pyridine,
2-[4'-(3"-hydroxypropoxy)phenyl]-6-[$^{131}$I]iodoimidazo[1,2-a]pyridine,
2-(4'-ethoxyphenyl)-6-[$^{123}$I]iodoimidazo[1,2-a]pyridine,
2-(4'-ethoxyphenyl)-6-[$^{125}$I]iodoimidazo[1,2-a]pyridine,
2-(4'-ethoxyphenyl)-6-[$^{131}$I]iodoimidazo[1,2-a]pyridine,
2-[3'-(2"-hydroxyethoxy)phenyl]-6-[$^{123}$I]iodoimidazo[1,2-a]pyridine,
2-[3'-(2"-hydroxyethoxy)phenyl]-6-[$^{125}$I]iodoimidazo[1,2-a]pyridine,
2-[3'-(2"-hydroxyethoxy)phenyl]-6-[$^{131}$I]iodoimidazo[1,2-a]pyridine,
2-[3'-(3"-hydroxypropoxy)phenyl]-6-[$^{123}$I]iodoimidazo[1,2-a]pyridine,
2-[3'-(3"-hydroxypropoxy)phenyl]-6-[$^{125}$I]iodoimidazo[1,2-a]pyridine,
2-[3'-(3"-hydroxypropoxy)phenyl]-6-[$^{131}$I]iodoimidazo[1,2-a]pyridine, or a salt thereof.

14. The diagnostic agent for Alzheimer's disease according to claim 9, wherein said diagnostic agent comprises a solution of said compound.

15. The diagnostic agent for Alzheimer's disease according to claim 9, wherein said diagnostic agent is a solution of said compound in water, physiological saline, or Ringer's solution.

16. The diagnostic agent for Alzheimer's disease according to claim 9, wherein said diagnostic agent comprises an intravenous dosage form that provides about 50 to 600 MBq per adult body weight of 60 kg.

* * * * *